United States Patent
Conrad et al.

(10) Patent No.: US 7,314,733 B2
(45) Date of Patent: Jan. 1, 2008

(54) SAITOHIN GENE AND USES OF SAME

(75) Inventors: Chris Conrad, Medford, MA (US); Peter Davies, Rye, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 129 days.

(21) Appl. No.: 10/495,545

(22) PCT Filed: Nov. 12, 2002

(86) PCT No.: PCT/US02/36315

§ 371 (c)(1), (2), (4) Date: Sep. 22, 2004

(87) PCT Pub. No.: WO03/042366

PCT Pub. Date: May 22, 2003

(65) Prior Publication Data

US 2005/0106567 A1 May 19, 2005

Related U.S. Application Data

(60) Provisional application No. 60/350,316, filed on Nov. 13, 2001.

(51) Int. Cl.
*A61K 38/00* (2006.01)
*C12P 21/00* (2006.01)
*C12P 21/02* (2006.01)
*C07K 1/00* (2006.01)

(52) U.S. Cl. ............... 435/69.1; 435/320.1; 435/252.8; 435/6; 435/91.2; 530/350; 536/23.5; 536/23.1; 536/24.31

(58) Field of Classification Search ................. None
See application file for complete search history.

(56) References Cited

U.S. PATENT DOCUMENTS 5,474,796 A 12/1995 Brennan
6,593,512 B1 * 7/2003 Vitek et al. .................... 800/18

FOREIGN PATENT DOCUMENTS

WO WO 99/62548 12/1999

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39, especially p. 36 at Box 2.*
Doerks et al., 1998, Trends in Genetics 14: 248-250.*
Smith et al., 1997, Nature Biotechnology 15:1222-1223.*
Brenner, 1999, Trends in Genetics 15:132-133.*
Bork et al., 1996, Trends in Genetics 12:425-427).*
Wang et al. Nuc. Acids Res. 27: 4609-4618, 1999.*
Kaufman et al. Blood. 1999; 94: 3178-3184.*
Wigley et al. Reprod Fert Dev. 1994; 6: 585-588.*
Campbell et al. Theriogenology. 1997; 47(1): 63-72.*
Phillips, A., J Pharm Pharmacology 53: 1169-1174, 2001.*
Cook et al. Annals of Neurol. 52: 690-691.*
Johansson et al. Neurodegener Dis. 2005; 2:28-35.*
Combarros et al. Dement Geriatr Cogn Disord. 2003; 16: 132-5.*
Peplonska et al. Neurosci Lett. 2003; 348: 163-6.*
Kerlavage, AR. The cerebellum II Homo sapiens cDNA 5' end, mRNA sequence EST28266. NCBI [online], Bethesda, MD, USA [retrieved on May 1, 2003]. Retrieved from NCBI, GenBankk Accession No. AA325304.
Conrad et al. A polymorphic gene nested within an intron of the tau gene: Implications for Alzheimer's disease. PNAS, May 2002, vol. 99, No. 11, pp. 7751-7756.
Poorkaj et al. A genomic sequence analysis of the mouse and human microtubule-associated protein tau. Mammalain Genome, 2001, vol. 12, pp. 700-712.
Streffer et al. Saitohin gene is not associated with Alzheimer's disease. J. Neurol. Neurosurg. Psychiatry, 2003, vol. 74, pp. 362-363.
Verpillat et al. Is the Saitohin gene involved in neurodegenerative disease? Ann. Neurol. 2002, vol. 52, pp. 829-832.
Birren, B et al. "Homo sapiens chromosome 17, clone—2524N8, complete sequence," Sep. 26, 1999. Database Accession No. AC010792. Abstract.
Kerlavage, AR, "The cerebellum II homo sapiens cDNA 5' end, mRNA sequence," Apr. 20, 1997. GenBank Acc: AA325304.
Bullido, M J et al., A polymorphism in the tau gene associated with risk for Alzheimer's disease. NeuroScience Letters 278 (1-2): 49-52, 2000.
Conrad C. et al. Molecular evolution and genetics of the Saitohin gene and tau haplotype in Alzheimer's disease and argyrophilic grain disease. Journal of Neurochemistry, 2004, 89, 179-188.
Gao L. et al. Saitohin, Which Is Nested in the tau Locus and Confers Allele-specific Susceptibility to Several Neurodegenerative Diseases, Interacts with Peroxiredoxin 6. The Journal of Biological Chemistry, vol. 280, No. 47, 39268-39272, 2005.
Conrad C et al. Saitohin, a novel putative gene in the tau locus. Society for Neuroscience Abstract, 2001.
Seripa D et al., entitled "Alzheimer disease risk associated with APOE4 is modified by STH gene polymorphism," Neurology 2004;62: pp. 1631-1633.

* cited by examiner

*Primary Examiner*—Eileen B. O'Hara
*Assistant Examiner*—Christina Borgeest
(74) *Attorney, Agent, or Firm*—Amster, Rothstein and Ebenstein LLP

(57) ABSTRACT

The present invention provides an isolated nucleic acid sequence encoding saitohin (STH), an isolated nucleic acid sequence that hybridizes to said sequence, and a purified protein encoded by said nucleic acid sequences. The present invention also provides a purified STH protein, and a method of making STH protein. The present invention is further directed to an antibody specific for STH, and a method for producing said antibody. Additionally, the present invention discloses a vector comprising a nucleic acid sequence encoding STH, a host cell transformed with said vector, and transgenic nonhuman animals. The present invention further provides methods for determining whether a subject has, or is at increased risk for developing, a neurodegenerative disease, and for assessing said subject's prognosis. Finally, the present invention discloses kits for determining whether a subject has, or is at increased risk for developing, a neurodegenerative disease.

34 Claims, 6 Drawing Sheets

A: nucleotide sequence of saitohin-Q gene tgccatctcctccaggaagtcttcctggattcccctctctcttcttaaagcccctgtaaactctgaccacactgagcatgtgtctg
ctgctccctagtctgggccatgagtgagggtggaggccaAgtctcatgcattttgcagcccccacaagactgtgcaggtgg
ccggccctcattgaatgcggggttaatttaactcagcctctgtgtgagtggatgattcaggttgccagagacagaaccctca
gcttagcatgggaagtagcttccctgttgaccctgagttcatctgaggttggcttggaaggtgtgggcaccatttggcccagtt
cttacagctctgaagagagcagcaggaatggggctgagcagggaagacaactttccattgaaggccccttcagggccag
aactgtccctcccaccctgcagctgccctgcctctgcccatgaggggtgagagtcaggcgacctcatgccaagtgtagaaa
ggggcagacgggagccccaggttatgacgtcaccatgctgggtggaggcagcacgtccaaatctactaaagggttaaag
gagaaagggtgacttgactttcttgagatattttggggacgaagtgtggaaaagtggcagaggacacagtcacagcctc
ccttaaatgccaggaaagcctagaaaaattgtctgaaactaaacctcagccataacaaagaccaacacatgaatctccag
gaaaaaagaaaaagaaaaatgtcatacagggtccatgcacaagagcctttaaaatgacccgctgaagggtgtcaggcct
cctcctcctggactggcctgaaggctccacgagcttttgctgagacctttgggtccctgtggcctcatgtagtacccagtatgc
agtaagtgctcaataaa

FIG. 1

A: nucleotide sequence of saitohin-R gene tgccatctcctccaggaagtcttcctggattcccctctctcttcttaaagcccctgtaaactctgaccacactgagcatgtgtctg
ctgctccctagtctgggccatgagtgagggtggaggccaGgtctcatgcattttgcagcccccacaagactgtgcaggtg
gccggccctcattgaatgcggggttaatttaactcagcctctgtgtgagtggatgattcaggttgccagagacagaaccctc
agcttagcatgggaagtagcttccctgttgaccctgagttcatctgaggttggcttggaaggtgtgggcaccatttggcccag
ttcttacagctctgaagagagcagcaggaatggggctgagcagggaagacaactttccattgaaggccccttcagggcca
gaactgtccctcccaccctgcagctgccctgcctctgcccatgaggggtgagagtcaggcgacctcatgccaagtgtagaa
aggggcagacgggagccccaggttatgacgtcaccatgctgggtggaggcagcacgtccaaatctactaaagggttaaa
ggagaaagggtgacttgactttcttgagatattttggggacgaagtgtggaaaagtggcagaggacacagtcacagcct
cccttaaatgccaggaaagcctagaaaaattgtctgaaactaaacctcagccataacaaagaccaacacatgaatctcca
ggaaaaaagaaaaagaaaaatgtcatacagggtccatgcacaagagcctttaaaatgacccgctgaagggtgtcaggcc
tcctcctcctggactggcctgaaggctccacgagcttttgctgagacctttgggtccctgtggcctcatgtagtacccagtatg
cagtaagtgctcaataaa

FIG. 2

B: amino acid sequence of saitohin-Q protein

MSEGGGQVSCIFAAPTRLCRWPALIECGVNLTQPLCEWMIQVARDRTLSLAWEVASLLTL
SSSEVGLEGVGTIWPSSYSSEESSRNGAEQGRQLSIEGPFQGQNCPSHPAAALPLPMRGES
QATSCQV

FIG. 3

B: amino acid sequence of saitohin-R protein

MSEGGGRVSCIFAAPTRLCRWPALIECGVNLTQPLCEWMIQVARDRTLSLAWEVASLLTL
SSSEVGLEGVGTIWPSSYSSEESSRNGAEQGRQLSIEGPFQGQNCPSHPAAALPLPMRGES
QATSCQV

FIG. 4

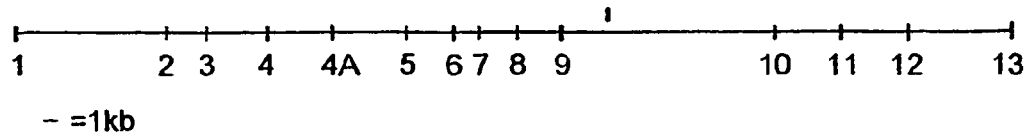

FIG. 6

```
1    /    1                                   31   /   11
ATG AGT GAG GGT GGA GGC CAA GTC TCA TGC  ATT TTT GCA GCC CCC ACA AGA CTG TGC AGG
met ser glu gly gly gly gln val ser cys  ile phe ala ala pro thr arg leu cys arg
61   /   21                                  91   /   31
TGG CCG GCC CTC ATT GAA TGC GGG GTT AAT  TTA ACT CAG CCT CTG TGT GAG TGG ATG ATT
trp pro ala leu ile glu cys gly val asn  leu thr gln pro leu cys glu trp met ile
121  /   41                                  151  /   51
CAG GTT GCC AGA GAC AGA ACC CTC AGC TTA  GCA TGG GAA GTA GCT TCC CTG TTG ACC CTG
gln val ala arg asp arg thr leu ser leu  ala trp glu val ala ser leu leu thr leu
181  /   61                                  211  /   71
AGT TCA TCT GAG GTT GGC TTG GAA GGT GTG  GGC ACC ATT TGG CCC AGT TCT TAC AGC TCT
ser ser ser glu val gly leu glu gly val  gly thr ile trp pro ser ser tyr ser ser
241  /   81                                  271  /   91
GAA GAG AGC AGC AGG AAT GGG GCT GAG CAG  GGA AGA CAA CTT TCC ATT GAA GGC CCC TTT
glu glu ser ser arg asn gly ala glu gln  gly arg gln leu ser ile glu gly pro phe
301  /   101                                 331  /   111
CAG GGC CAG AAC TGT CCC TCC CAC CCT GCA  GCT GCC CTG CCT CTG CCC ATG AGG GGT GAG
gln gly gln asn cys pro ser his pro ala  ala ala leu pro leu pro met arg gly glu
361  /   121
AGT CAG GCG ACC TCA TGC CAA GTG TAG
ser gln ala thr ser cys gln val AMB
```

FIG. 7

FIG. 8A
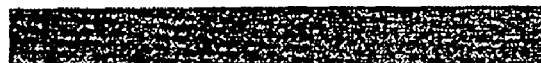
FIG. 8B
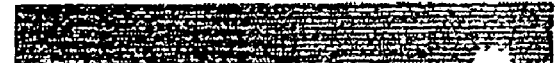

SEQUENCE LISTING

<160> NUMBER OF SEQ ID NOS: 8

<210> SEQ ID NO 1
<211> LENGTH: 915
<212> TYPE: DNA
<213> ORGANISM: Homo sapiens (sequence of saitohin-Q gene)

<400> SEQUENCE: 1

```
tgccatctcc tccaggaagt cttcctggat tccctctct cttcttaaag ccctgtaaa     60 ctctgaccac actgagcatg tgtctgctgc tccctagtct gggccatgag tgagggtgga    120
ggccaagtct catgcatttt tgcagccccc acaagactgt gcaggtggcc ggccctcatt    180
gaatgcgggg ttaatttaac tcagcctctg tgtgagtgga tgattcaggt tgccagagac    240
agaaccctca gcttagcatg ggaagtagct tccctgttga ccctgagttc atctgaggtt    300
ggcttggaag gtgtgggcac catttggccc agttcttaca gctctgaaga gagcagcagg    360
```

```
aatgggctg agcagggaag acaactttcc attgaaggcc cctttcaggg ccagaactgt      420
ccctcccacc ctgcagctgc cctgcctctg cccatgaggg gtgagagtca ggcgacctca     480
tgccaagtgt agaaagggc agacgggagc ccaggttat gacgtcacca tgctgggtgg      540
aggcagcacg tccaaatcta ctaaagggtt aaggagaaa gggtgacttg acttttcttg     600
agatattttg ggggacgaag tgtggaaaag tggcagagga cacagtcaca gcctccctta   660
aatgccagga aagcctagaa aaattgtctg aaactaaacc tcagccataa caaagaccaa   720
cacatgaatc tccaggaaaa aagaaaaaga aaaatgtcat acagggtcca tgcacaagag   780
cctttaaaat gacccgctga agggtgtcag gcctcctcct cctggactgg cctgaaggct   840
ccacgagctt ttgctgagac ctttgggtcc ctgtggcctc atgtagtacc cagtatgcag   900
taagtgctca ataaa                                                    915

<210> SEQ ID NO 2
<211> LENGTH: 915
<212> TYPE: DNA
<213> ORGANISM: Homo sapiens (sequence of saitohin-R gene)

<400> SEQUENCE: 2
tgccatctcc tccaggaagt cttcctggat tcccctctct cttcttaaag cccctgtaaa     60
ctctgaccac actgagcatg tgtctgctgc tccctagtct gggccatgag tgagggtgga   120
ggccaggtct catgcatttt tgcagcccc acaagactgt gcaggtggcc ggccctcatt    180
gaatgcgggg ttaatttaac tcagcctctg tgtgagtgga tgattcaggt tgccagagac   240
agaaccctca gcttagcatg ggaagtagct tccctgttga ccctgagttc atctgaggtt   300
ggcttggaag gtgtgggcac catttggccc agttcttaca gctctgaaga gagcagcagg   360 aatgggctg agcagggaag acaactttcc attgaaggcc cctttcaggg ccagaactgt     420
ccctcccacc ctgcagctgc cctgcctctg cccatgaggg gtgagagtca ggcgacctca    480
tgccaagtgt agaaagggc agacgggagc ccaggttat gacgtcacca tgctgggtgg     540
aggcagcacg tccaaatcta ctaaagggtt aaggagaaa gggtgacttg acttttcttg    600
agatattttg ggggacgaag tgtggaaaag tggcagagga cacagtcaca gcctccctta   660
aatgccagga aagcctagaa aaattgtctg aaactaaacc tcagccataa caaagaccaa   720
cacatgaatc tccaggaaaa aagaaaaaga aaaatgtcat acagggtcca tgcacaagag   780
cctttaaaat gacccgctga agggtgtcag gcctcctcct cctggactgg cctgaaggct   840
ccacgagctt ttgctgagac ctttgggtcc ctgtggcctc atgtagtacc cagtatgcag   900
taagtgctca ataaa                                                    915

<210> SEQ ID NO 3
<211> LENGTH: 128
<212> TYPE: PRT
<213> ORGANISM: Homo sapiens (sequence of saitohin-Q protein)

<400> SEQUENCE: 3

Met Ser Glu Gly Gly Gly Gln Val Ser Cys Ile Phe Ala Ala Pro Thr
1               5                  10                  15

Arg Leu Cys Arg Trp Pro Ala Leu Ile Glu Cys Gly Val Asn Leu Thr
            20                  25                  30

Gln Pro Leu Cys Glu Trp Met Ile Gln Val Ala Arg Asp Arg Thr Leu
        35                  40                  45

Ser Leu Ala Trp Glu Val Ala Ser Leu Leu Thr Leu Ser Ser Ser Glu
    50                  55                  60
```

Val Gly Leu Glu Gly Val Gly Thr Ile Trp Pro Ser Ser Tyr Ser Ser
65                  70                  75                  80

Glu Glu Ser Ser Arg Asn Gly Ala Glu Gln Gly Arg Gln Leu Ser Ile
            85                  90                  95

Glu Gly Pro Phe Gln Gly Gln Asn Cys Pro Ser His Pro Ala Ala Ala
        100                 105                 110

Leu Pro Leu Pro Met Arg Gly Glu Ser Gln Ala Thr Ser Cys Gln Val
        115                 120                 125

<210> SEQ ID NO 4
<211> LENGTH: 128
<212> TYPE: PRT
<213> ORGANISM: Homo sapiens (sequence of saitohin-R protein)

<400> SEQUENCE: 4

Met Ser Glu Gly Gly Gly Arg Val Ser Cys Ile Phe Ala Ala Pro Thr
1               5                   10                  15

Arg Leu Cys Arg Trp Pro Ala Leu Ile Glu Cys Gly Val Asn Leu Thr
            20                  25                  30

Gln Pro Leu Cys Glu Trp Met Ile Gln Val Ala Arg Asp Arg Thr Leu
        35                  40                  45

Ser Leu Ala Trp Glu Val Ala Ser Leu Leu Thr Leu Ser Ser Ser Glu
    50                  55                  60

Val Gly Leu Glu Gly Val Gly Thr Ile Trp Pro Ser Ser Tyr Ser Ser
65                  70                  75                  80

Glu Glu Ser Ser Arg Asn Gly Ala Glu Gln Gly Arg Gln Leu Ser Ile
            85                  90                  95

Glu Gly Pro Phe Gln Gly Gln Asn Cys Pro Ser His Pro Ala Ala Ala
        100                 105                 110

Leu Pro Leu Pro Met Arg Gly Glu Ser Gln Ala Thr Ser Cys Gln Val
        115                 120                 125

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
ccctgtaaac tctgaccaca c                                          21

<210> SEQ ID NO 6
<211> LENGTH: 21
<212> TYPE: DNA
<213> ORGANISM: artificial
<220> FEATURE:
<223> OTHER INFORMATION: primer

<400> SEQUENCE: 6
catgggaagt agcttccctg t                                          21

<210> SEQ ID NO 7
<211> LENGTH: 27
<212> TYPE: DNA
<213> ORGANISM: artificial
<220> FEATURE:
<223> OTHER INFORMATION: primer

<400> SEQUENCE: 7
gccaacgcca ccaggattcc agcaaaa                                    27

```
<210> SEQ ID NO 8
<211> LENGTH: 21
<212> TYPE: DNA
<213> ORGANISM: artificial
<220> FEATURE:
<223> OTHER INFORMATION: primer

<400> SEQUENCE: 8
tttacttcca cctggccacc t                                              21
```

SAITOHIN GENE AND USES OF SAME

This application is a national stage entry under 35 U.S.C. §371 of PCT International Application No. PCT/US02/36315, filed Nov. 12, 2002, which claims priority of U.S. Provisional Patent Application No. 60/350,316, filed Nov. 13, 2001.

STATEMENT OF GOVERNMENT INTEREST

This invention was made with government support under NIMH Grant No. 38623. As such, the United States government has certain rights in this invention.

BACKGROUND OF THE INVENTION

Alzheimer's disease (AD) is a neurodegenerative disease characterized by a progressive, inexorable loss of cognitive function (1). AD is the most common late-onset dementia, affecting several million people in the developed countries of the world. Approximately 4 million Americans suffer from Alzheimer's disease, at an annual cost of about $100 billion, making AD the third most costly disorder of aging. The disease is about twice as common in women as in men, and accounts for more than 65% of the dementias in the elderly. Early identification is critical in progressive conditions such as AD, because earlier treatment may be more effective than later treatment in preserving cognitive function. Furthermore, early detection may allow time to explore options for treatment and care. To date, however, a cure for Alzheimer's disease is not available, and cognitive decline is inevitable.

AD has two major neuropathological hallmarks: extracellular aggregates, called amyloid plaques, neuritic plaques, or senile plaques, which are composed of neurites, astrocytes, and glial cells around an amyloid core, and which are located in the cerebral cortex; and intracellular aggregates, called neurofibrillary tangles, which are composed of paired helical filaments). While senile plaques and neurofibrillary tangles occur with normal aging, they are much more prevalent in persons with Alzheimer's disease. Although the processes of AD could be triggered by many environmental insults, genetic studies have shown that mutations and polymorphisms of particular genes can confer susceptibility to this degenerative process.

Genetic studies of Alzheimer's disease patients have identified several early onset (<65 years old) disease risk factors (e.g., mutations in the amyloid precursor protein, Presenilin 1 and Presenilin 2), and a late-onset (>65 years old) disease risk factor, the E4 allele of apolipoprotein E (ApoE4) (see, e.g., U.S. Pat. Nos. 5,716,828; 5,767,248; and 6,136,530). In the late-onset AD (LOAD) population, only 50% of the subjects have been shown to carry the ApoE4 allele, which is compelling evidence to support the existence of additional genetic risk factors associated with AD. Indeed, recent linkage studies of LOAD-affected sibling pairs have identified loci on chromosomes 9 and 10 that may harbor risk-factor genes (2).

To date, the known risk factors for AD have been shown to modulate amyloid production or deposition; yet, none is necessary or sufficient for the diagnosis of AD, and none has demonstrated a role in the formation of neurofibrillary tangles (NFT). Extensive research on NFT has been undertaken in conjunction with studies on the conversion of tau, a protein that is normally soluble, into a hyperphosphorylated insoluble protein that is detected in NFT. Tau, a microtubule-associate protein is important in establishing and maintaining neuronal morphology. In addition to its role in normal cells, tau protein is involved in many neurodegenerative diseases, including AD, as the main component of intraneuronal aggregates. Some of the more common diseases with tau pathology include frontotemporal dementia (FTD), Pick's disease, and progressive supranuclear palsy (PSP) (3). The involvement of tau in these disorders has prompted much investigation into its function and role in the progression of these disorders.

Recently, several tau-coding mutations have been shown to segregate with FTD, and there have been some intriguing results with transgenic mice expressing the FTD-tau mutation, P301L, that develop tau aggregates (3, 4). However, in AD, no mutations have been found in the tau gene, suggesting that other factors are likely involved in the formation of tau aggregates. These factors could have implications for other neurodegenerative disorders with tau pathology (5-9).

In FTD and PSP subjects, recent genetic studies of the tau locus have shown that several mutations and a polymorphism segregate with these disorders, respectively (3). The identification and investigation of neighboring genes in the tau locus could be valuable in the study of molecular genetic risk factors in PSP, since there have been no reported tau coding or intronic mutations (10). This information could also be useful, not only for PSP, but for other neurodegenerative diseases, such as AD. The identification of new risk factors associated with AD and other neurodegenerative diseases may assist in the diagnosis of such diseases facilitate future preventive and therapeutic measures directed to these diseases.

SUMMARY OF THE INVENTION

The present invention is predicated on the identification of a novel gene, saitohin (STH), within the tau locus, and the observation that the saitohin-R (STH-R) allele of the STH gene is associated with an increased risk of developing Alzheimer's disease ("AD"). On the basis of these findings, it is an object of the present invention to provide an isolated nucleic acid sequence encoding saitohin (STH), including both the STH-Q and STH-R alleles, and an isolated nucleic acid sequence that hybridizes under high stringency conditions to a second nucleic acid that is complementary to a nucleic acid sequence encoding STH.

The present invention also discloses a purified saitohin (STH) protein, including both the STH-Q and STH-R isoforms, and a purified protein encoded by a nucleic acid sequence that hybridizes under high stringency conditions to a second nucleic acid sequence that is complementary to a nucleic acid sequence encoding STH, including both the STH-Q and STH-R alleles. Also provided is a method of making STH protein, including both the STH-Q and STH-R isoforms.

The present invention is further directed to an antibody specific for saitohin (STH) protein, including both the STH-Q and STH-R isoforms, and a method for producing an antibody specific for STH protein, including both the STH-Q and STH-R isoforms.

Additionally, the present invention discloses a vector comprising a nucleic acid sequence encoding saitohin (STH), including both the STH-Q and STH-R alleles, and a host cell transformed with a vector comprising a nucleic acid sequence encoding STH, including both the STH-Q and STH-R alleles.

The present invention is also directed to a transgenic non-human animal whose genome comprises a disruption in its endogenous STH gene, and a transgenic non-human animal that overexpresses saitohin (STH) protein, including both the STH-Q and STH-R isoforms.

The present invention further provides a method for determining whether a subject has a neurodegenerative disease or is at increased risk for developing neurodegenerative disease, comprising assaying a diagnostic sample of the subject for the presence of one or more alleles of saitohin (STH), wherein detection of the presence of STH-R allele is indicative that the subject has, or is at increased risk for developing, a neurodegenerative disease.

The present invention also provides a method for assessing the prognosis of a subject who has, or may develop, a neurodegenerative disease, comprising assaying a diagnostic sample of the subject for the presence of one or more alleles of saitohin (STH), wherein the presence of two STH-R alleles in the diagnostic sample of the subject indicates a more negative prognosis for the subject.

Finally, the present invention discloses kits for determining whether a subject has a neurodegenerative disease or is at increased risk for developing a neurodegenerative disease.

Additional objects of the present invention will be apparent in view of the description which follows.

BRIEF DESCRIPTION OF THE FIGURES

FIG. 1 depicts the nucleotide sequence of the saitohin-Q (STH-Q) gene (SEQ ID NO:1). The protein start (atg) and stop (tag) codons are underlined. The nucleotide sequence of STH-Q differs from that of saitohin-R at the $126^{th}$ nucleotide which, in STH-Q, is A (capitalized and bolded).

FIG. 2 depicts the nucleotide sequence of the saitohin-R (STH-R) gene (SEQ ID NO:2). The protein start (atg) and stop (tag) codons are underlined. In STH-R, the $126^{th}$ nucleotide is G (capitalized and bolded).

FIG. 3 sets forth the predicted amino acid sequence of the STH-Q protein (SEQ ID NO:3). The $126^{th}$ nucleotide of the STH-Q gene results in a Q (glutamine) at position seven of the STH-Q protein.

FIG. 4 shows the predicted amino acid sequence of the STH-R protein (SEQ ID NO:4). The difference in the $126^{th}$ nucleotide of the STH-Q and STH-R genes changes the Q (glutamine) in the STH-Q protein to an R (arginine) in the STH-R protein.

FIG. 6 illustrates the tau locus and the physical location of the saitohin gene (vertical bar, above) within the intron downstream of exon 9 of the tau gene.

FIG. 7 depicts the open reading frame for the STH protein. The predicted amino acids (SEQ ID NO:3) (three-letter abbreviation) for the nucleotide sequences (nucleotides 106-492 of SEQ ID NO:1) are shown. At the boxed glutamine (gin) codon [C A A] at amino acid 7, the nucleotide polymorphism (A→G) changes the codon [C G A] to an arginine in the STH protein.

DETAILED DESCRIPTION OF THE INVENTION

Figure 5:
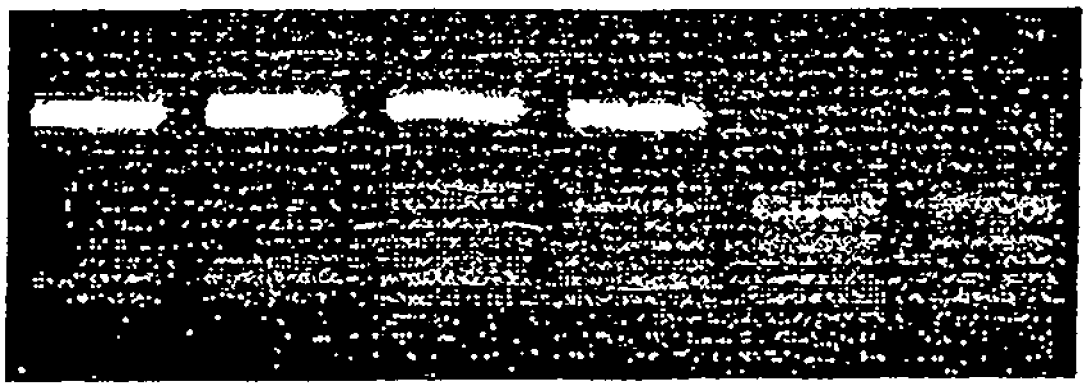
FIG. 5 sets forth a representative alleleotyping gel of HinFI-digested PCR products of the genotypes QQ, QR, and RR, according to methods described below. The polymorphism creates a novel HinF1 restriction enzyme site. HinF1-digested PCR product yields two bands (at 171 bp and 55 bp) in subjects with a Q allele, and three bands (at 55 bp, 74 bp, and 97 bp) in individuals with an R allele. Two QQ homozygotes, two QR heterozygotes, and two RR homozygotes are shown.

The present invention is directed to a novel gene, saitohin (STH), that is located on chromosome 17, within an intron of the gene encoding the microtubule-associated protein, tau. As disclosed herein, the saitohin gene exists in at least two forms, or alleles, in the human population. In one form, referred to herein as "saitohin-Q (STH-Q)", the $126^{th}$ nucleotide is A, which results in a Q (glutamine) at position seven of the STH-Q isoform of the STH protein. In the second form of STH, referred to herein as "saitohin-R (STH-R)", the $126^{th}$ nucleotide is G, which results in an R (arginine) at position seven of the STH-R isoform of the STH protein.

Accordingly, the present invention provides a saitohin (STH) gene, and an isolated nucleic acid sequence encoding STH protein. The STH gene, and the nucleic acid sequence encoding STH protein, include both the STH-Q and STH-R alleles. The STH gene may be an "endogenous" STH gene, which is one that originates or arises naturally, from within an organism. Due to the degeneracy of the genetic code, the STH gene of the present invention includes a multitude of nucleic acid substitutions which will also encode STH protein, including both the STH-Q and STH-R isoforms. As used herein, an "STH protein" includes, where appropriate, both an STH protein (including both STH-Q and STH-R isoforms) and an "STH analogue". Unless otherwise indicated, "protein" shall mean a protein, protein domain, polypeptide, or peptide. An "STH analogue" may be any protein having functional similarity to the STH protein that is 60% or greater (preferably, 70% or greater) in amino-acid-sequence homology with the STH protein.

The nucleic acid sequence of the present invention may be genomic DNA, cDNA, RNA, antisense DNA, or antisense RNA, and may be derived from any species. The nucleic acid sequence of the present invention is preferably derived from a mammalian species, and, more preferably, from a human.

The nucleic acid sequence of the present invention may be the Q allele of STH, referred to herein as "saitohin-Q (STH-Q)", in which the $126^{th}$ nucleotide is A, which results in a Q (glutamine) at position seven of the STH-Q protein. Where the nucleic acid sequence is the STH-Q allele, said nucleic acid sequence preferably comprises the nucleotide sequence of FIG. 1 (including conservative substitutions thereof). "Conservative substitutions", as used herein, are those amino acid substitutions which are functionally equivalent to the substituted amino acid residue, either because they have similar polarity or steric arrangement, or because they belong to the same class as the substituted residue (e.g., hydrophobic, acidic, or basic). The nucleic acid of the present invention may encode the STH-Q isoform of the STH protein, comprising the amino acid sequence set forth in FIG. 3.

The present invention further provides an isolated nucleic acid sequence that hybridizes, preferably under high stringency conditions (e.g., hybridization to filter-bound DNA in 0.5-M $NaHPO_4$ at 65° C. and washing in 0.1×SSC/0.1% SDS at 68° C.) or moderate stringency conditions (e.g., washing in 0.2×SSC/0.1% SDS at 42° C.) (13), to a second nucleic acid that is complementary to the nucleotide sequence set forth in FIG. 1 or a contiguous fragment thereof. In addition, the present invention provides a nucleic acid sequence encoding the STH-Q isoform of the STH protein having one or more mutations, wherein the mutations result in the expression of either a non-functional or mutant protein, or in a lack of expression altogether. The mutations may be generated by at least one of the methods selected from the group consisting of point mutation, insertion mutation, rearrangement, or deletion mutation, or a combination thereof.

The nucleic acid sequence of the present invention may be the R allele of STH, referred to herein as "saitohin-R (STH-R)", in which the $126^{th}$ nucleotide is G, which results in an R (arginine) at position seven of the STH-R isoform of the STH protein. Where the nucleic acid sequence is the STH-R allele, said nucleic acid sequence preferably comprises the nucleotide sequence of FIG. 2 (including conservative substitutions thereof). The nucleic acid of the present invention may encode the STH-R isoform of the STH protein, comprising the amino acid sequence set forth in FIG. 4.

The present invention further discloses an isolated nucleic acid sequence that hybridizes, preferably under high stringency conditions (e.g., hybridization to filter-bound DNA in 0.5-M $NaHPO_4$ at 65° C. and washing in 0.1×SSC/0.1% SDS at 68° C.) or moderate stringency conditions (e.g., washing in 0.2×SSC/0.1% SDS at 42° C.) (2), to a second nucleic acid that is complementary to the nucleotide sequence set forth in FIG. 2 or a contiguous fragment thereof. In addition, the present invention provides a nucleic acid sequence encoding the STH-R isoform of the STH protein having one or more mutations, wherein the mutations result in the expression of either a non-functional or mutant protein, or in a lack of expression altogether. The mutations may be generated by at least one of the methods selected from the group consisting of point mutation, insertion mutation, rearrangement, or deletion mutation, or a combination thereof.

The present invention also provides an isolated and purified STH protein. The STH protein may be isolated from tissue (e.g., brain tissue) obtained from a subject, or recombinantly produced as described below. The STH protein includes both the STH-Q and STH-R isoforms disclosed herein.

The protein of the present invention may be the Q isoform of the STH protein, or saitohin-Q (STH-Q), in which there is a Q (glutamine) at position seven. Where the protein is the STH-Q isoform, said protein preferably comprises the amino acid sequence set forth in FIG. 3. Alternatively, the STH-Q isoform of the STH protein may be encoded by the nucleotide sequence set forth in FIG. 1. The present invention is further directed to a purified protein encoded by a nucleic acid sequence that hybridizes under high stringency or moderate stringency conditions to a second nucleic acid sequence that is complementary to the nucleotide sequence set forth in FIG. 1 or a contiguous fragment thereof.

The protein of the present invention also may be the R isoform of the STH protein, or saitohin-R (STH-R), in which there is an R (arginine) at position seven. Where the protein is the STH-R isoform, said protein preferably comprises the amino acid sequence set forth in FIG. 4. Alternatively, the STH-Q isoform of the STH protein may be encoded by the nucleotide sequence set forth in FIG. 2. The present invention is further directed to a purified protein encoded by a nucleic acid sequence that hybridizes under high stringency or moderate stringency conditions to a second nucleic acid sequence that is complementary to the nucleotide sequence set forth in FIG. 2 or a contiguous fragment thereof.

Additionally, the present invention provides agents that bind to an STH protein, including both the STH-Q and STH-R isoforms of said STH protein. The agent may include, without limitation, an antibody, a compound, a drug, a Fab fragment, a $F(ab')_2$ fragment, a molecule, a nucleic acid, a protein (including a growth factor), a polypeptide, a peptide, a nucleic acid (including DNA, RNA, mRNA, antisense RNA), and any combinations thereof. Furthermore, the agent that binds to the STH protein, including both the STH-Q and STH-R isoforms, may be either natural or synthetic. A Fab fragment is a univalent antigen-binding fragment of an antibody, which is produced by papain digestion. A $F(ab')_2$ fragment is a divalent antigen-binding fragment of an antibody, which is produced by pepsin digestion. Agents that bind to the STH protein may be identified or screened by contacting the protein with the agent of interest, and assessing the ability of the agent to bind to the protein.

The agent of the present invention is preferably an antibody specific for, or immunoreactive with, STH protein, including the STH-Q and the STH-R isoforms. The antibody of the present invention may be monoclonal or polyclonal, and may be produced by techniques well known to those skilled in the art. The antibody of the present invention may be incorporated into kits which include an appropriate labeling system, buffers, and other necessary reagents for use in a variety of detection and diagnostic applications. Labeling of the antibody of the present invention may be accomplished by standard techniques using one of the variety of different chemiluminescent and radioactive labels known in the art.

The present invention further provides a method for producing an antibody specific for the STH protein, including both the STH-Q and STH-R isoforms, comprising the steps of: (a) immunizing a mammal with STH protein (e.g., STH-Q or STH-R); and (b) purifying antibody from a tissue of the mammal or from a hybridoma made using tissue of the mammal. For example, a polyclonal antibody may be produced by immunizing a rabbit, mouse, or rat with purified STH (e.g., STH-Q or STH-R). Thereafter, a monoclonal antibody may be produced by removing the spleen from the immunized rabbit, mouse, or rat, and fusing the spleen cells with myeloma cells to form a hybridoma which, when grown in culture, will produce a monoclonal antibody. Also provided is an antibody produced by this method.

The present invention further discloses agents that bind to a nucleic acid encoding STH protein, including both the STH-Q and STH-R alleles. Suitable agents include, but are not limited to, an antibody, a compound, a drug, a Fab fragment, a F(ab')$_2$ fragment, a molecule, a nucleic acid, a protein, a polypeptide, a peptide, a nucleic acid (including DNA, RNA, mRNA, antisense RNA), and any combinations thereof. The agents that bind to the nucleic acid encoding STH may inhibit or promote expression of the nucleic acid. Such agents may be discovered by a method for screening for an agent that binds to a nucleic acid encoding STH (e.g., the STH-Q allele or the STH-R allele), comprising contacting the nucleic acid with an agent of interest, and assessing the ability of the agent to bind to the nucleic acid. An agent that inhibits or promotes the expression of a nucleic acid encoding STH may be screened by contacting a host cell transformed with a vector comprising the nucleic acid, and assessing the agent's effect on expression of the nucleic acid.

The present invention also provides nucleic acid probes and mixtures thereof that hybridize to nucleic acid encoding STH protein, including both the STH-Q and STH-R alleles. Such probes may be prepared by a variety of techniques known to those skilled in the art, including, without limitation, PCR and restriction-enzyme digestion of nucleic acid encoding STH (e.g., the STH-Q allele or the STH-R allele); and automated synthesis of oligonucleotides whose sequences correspond to selected portions of the nucleotide sequence of nucleic acid encoding STH, using commercially-available oligonucleotide synthesizers such as the Applied Biosystems Model 392 DNA/RNA synthesizer.

The nucleic acid probes of the present invention also may be prepared so that they contain at least one point, insertion, rearrangement, or deletion mutation, or a combination thereof, to correspond to mutations of the STH gene.

The nucleic acid probes of the present invention may be DNA or RNA, and may vary in length from about 8 nucleotides to the entire length of the nucleic acid encoding STH (e.g., the STH-Q allele or the STH-R allele). Preferably, the probes are 8 to 30 nucleotides in length. Labeling of the nucleic acid probes may be accomplished using one of a number of methods known in the art, including, without limitation, PCR, nick translation, end labeling, fill-in end labeling, polynucleotide kinase exchange reaction, random priming, or SP6 polymerase (for riboprobe preparation), and one of a variety of labels, including, without limitation, radioactive labels such as $^{35}$S, $^{32}$P, or $^{3}$H and nonradioactive labels such as biotin, fluorescein (FITC), acridine, cholesterol, or carboxy-X-rhodamine (ROX). Combinations of two or more nucleic probes, corresponding to different or overlapping regions of nucleic acid encoding STH, also may be included in kits for use in a variety of detection and diagnostic applications.

The present invention is further directed to a vector comprising a nucleic acid sequence encoding STH protein. The nucleic acid sequence encoding STH protein may, for example, be the STH-Q allele or the STH-R allele. Where the nucleic acid sequence of the vector is the STH-Q allele, said nucleic acid sequence may comprise the nucleotide sequence of FIG. 1 or a contiguous fragment thereof. Alternatively, the nucleic acid sequence of the vector may comprise a nucleic acid sequence that hybridizes under high stringency or moderate stringency conditions to a nucleic acid sequence that is complementary to the nucleotide sequence set forth in FIG. 1, or to a contiguous fragment thereof. Where the nucleic acid sequence of the vector is the STH-R allele, said nucleic acid sequence may comprise the nucleotide sequence of FIG. 2 or a contiguous fragment thereof. Alternatively, the nucleic acid sequence of the vector may comprise a nucleic acid sequence that hybridizes under high stringency or moderate stringency conditions to a nucleic acid sequence that is complementary to the nucleotide sequence set forth in FIG. 2, or to a contiguous fragment thereof.

The vector of the present invention may be constructed by inserting nucleic acid encoding STH (e.g., the STH-Q or the STH-R allele) into a suitable vector nucleic acid operably linked to an expression control sequence, as described below. The term "inserted", as used herein, means the ligation of a foreign DNA fragment with vector DNA, by techniques such as the annealing of compatible cohesive ends generated by restriction endonuclease digestion, or by the use of blunt-end ligation techniques. Other methods of ligating DNA molecules will be apparent to one skilled in the art.

The vector of the present invention may be derived from a number of different sources, including plasmids, viral-derived nucleic acids, lyric bacteriophage derived from phage lambda, cosmids, or filamentous single-stranded bacteriophages such as M13. Depending upon the type of host cell into which the vector is introduced, vectors may be bacterial or eukaryotic. Bacterial vectors are derived from many sources, including the genomes of plasmids and phages. Eukaryotic vectors are constructed from a number of different sources, e.g., yeast plasmids and viruses. Some vectors, referred to as shuttle vectors, are capable of replicating in both bacteria and eukaryotes. The nucleic acid from which the vector is derived is usually greatly reduced in size, such that only those genes essential for its autonomous replication remain. This reduction in size enables the vectors to accommodate large segments of foreign DNA. Examples of suitable vectors into which nucleic acid encoding STH (e.g., the STH-Q or the STH-R allele) can be inserted include, but are not limited to, pCGS, pBR322, pUC18, pUC19, pHSV-106, pJS97, pJS98, M13 mp18, M13 mp19, pSPORT 1, pGem, pSPORT 2, pSV●SPORT 1, pBluescript II, λZapII, λgt10, λgt11, λgt22A, and λZIPLOX. Other suitable vectors will be obvious to one skilled in the art.

The vector of the present invention may be introduced into a host cell. Accordingly, the present invention further provides a host cell transformed with the vector of the present invention. The term "host cell", as used herein, means the bacterial or eukaryotic cell into which the vector is introduced. The term "transform" denotes the introduction of a vector into a bacterial or eukaryotic host cell. Additionally, as used herein, the term "introduction" is a general term indicating that one of a variety of means has been used to allow the vector to enter the intracellular environment of the host cell in such a way that the nucleic acid exists in stable form, and may be expressed, therein. As such, it encompasses transformation of bacterial cells, as well as transfection, transduction, and related methods in eukaryotic cells. The vector of the present invention may exist in integrated or unintegrated form within the host cell. When in unintegrated form, the vector is capable of autonomous replication.

Any one of a number of suitable bacterial or eukaryotic host cells may be transformed with the vector of the present invention. Examples of suitable host cells are known to one skilled in the art, and include, without limitation, bacterial cells such as *Escherichia coli* strains c600, c600hfl, HB101, LE392, Y1090, JM103, JM109, JM101, JM107, Y1088, Y1089, Y1090, Y1090(ZZ), DM1, PH10B, DH11S, DH125, RR1, TB1 and SURE, *Bacillus subtilis, Agrobacterium tumefaciens, Bacillus megaterium*; and eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator*, cultured insect cells, cultured chicken fibroblasts, cultured hamster cells, cultured human cells such as HT1080, MCF7, and 143B, and cultured mouse cells such as EL4 and NIH3T3 cells.

Some bacterial and eukaryotic vectors have been engineered so that they are capable of expressing inserted nucleic acids to high levels within the host cell. An "expression cassette" or "expression control sequence", comprising nucleic acid encoding a STH protein (e.g., the STH-Q or the STH-R allele) operably linked or under the control of transcriptional and translational regulatory elements (e.g., a promoter, ribosome binding site, operator, or enhancer), can be made and used for expression of STH protein (e.g., the STH-Q or the STH-R isoform) in vitro or in vivo. As used herein, "expression" refers to the ability of the vector to transcribe the inserted nucleic acid into mRNA, so that synthesis of the protein encoded by the inserted nucleic acid can occur. The choice of regulatory elements employed may vary, depending on such factors as the host cell to be transformed and the desired level of expression.

For example, in vectors used for the expression of a gene in a bacterial host cell such as *Escherichia coli*, the lac operator-promoter or the tac promoter is often used. Eukaryotic vectors use promoter-enhancer sequences of viral genes, especially those of tumor viruses. Several promoters for use in mammalian cells are known in the art. Examples of these promoters include, without limitation, the phosphoglycerate (PGK) promoter, the simian virus 40 (SV40) early promoter, the Rous sarcoma virus (RSV) promoter, the adenovirus major late promoter (MLP), and the human cytomegalovirus (CMV) immediate early 1 promoter. However, any promoter that facilitates suitable expression levels can be used in the present invention. Inducible promoters (e.g., those obtained from the heat shock gene, metallothionine gene, beta-interferon gene, or steroid hormone responsive genes, including, without limitation, the lac operator-promoter in *E. coli* and metallothionine or mouse mammary tumor virus promoters in eukaryotic cells) may be useful for regulating transcription based on external stimuli.

Vectors suitable for expression in a host cell of nucleic acid encoding STH (e.g., the STH-Q or the STH-R allele) are well-known to one skilled in the art, and include pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVL1392 (Invitrogen), pCDM8 (Invitrogen), pcDNA 1 (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors will be apparent to one skilled in the art.

The vector of the present invention may be introduced into a host cell using conventional procedures known in the art, including, without limitation, electroporation, DEAE Dextran transfection, calcium phosphate rransfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. For the purposes of gene transfer into a host cell, tissue, or subject, a recombinant vector containing nucleic acid encoding STH (e.g., the STH-Q or the STH-R allele) may be combined with a sterile aqueous solution that is preferably isotonic with the blood of the recipient. Such formulations may be prepared by suspending the recombinant vector in water containing physiologically-compatible substances, such as sodium chloride, glycine, and the like, and having buffered pH compatible with physiological conditions, to produce an aqueous solution, then rendering the solution sterile. In a preferred embodiment of the invention, the recombinant vector is combined with a 20-25% sucrose in saline solution in preparation for introduction into a mammal.

The present invention further provides a method of making recombinant STH protein, comprising the steps of: (a) introducing into a suitable bacterial or eukaryotic host cell a nucleic acid sequence encoding STH (e.g., the STH-Q or the STH-R allele), or a nucleic acid that hybridizes under high stringency conditions or moderate stringency conditions to a second nucleic acid that is complementary to the nucleotide sequence set forth in FIG. 1 or a contiguous fragment thereof, or a nucleic acid that hybridizes under high stringency conditions or moderate stringency conditions to a second nucleic acid that is complementary to the nucleotide sequence set forth in FIG. 2 or a contiguous fragment thereof; (b) maintaining the host cell under conditions such that the nucleic acid sequence is expressed to produce STH protein (e.g., the STH-Q isoform or the STH-R isoform); and (c) recovering the recombinant STH protein from the culture medium, from the host cells, or from cell lysate. As used herein, the term "recombinant" refers to STH protein (e.g., the STH-Q isoform or the STH-R isoform) produced by purification from a host cell transformed with a vector capable of directing its expression to a high level. In the method of the present invention, a nucleic acid sequence encoding STH (e.g., the STH-Q allele or the STH-R allele) may be introduced into a suitable host cell by any of the above-described methods.

A variety of methods of growing host cells transformed with a vector are known to those skilled in the art. The type of host cell (i.e., bacterial or eukaryotic) is the primary determinant of both the method to be utilized and the optimization of specific parameters relating to such factors as temperature, trace nutrients, humidity, and growth time. Depending on the vector used, the host cells may have to be induced by the addition of a specific compound at a certain point in the growth cycle, in order to initiate expression of the nucleic acid contained in the vector. Examples of compounds used to induce expression of the nucleic acid contained in the vector are known to one skilled in the art, and include, without limitation, IPTG, zinc, and dexamethasone. Using standard methods of protein isolation and purification, such as ammonium sulfate precipitation and subsequent dialysis to remove salt, followed by fractionation according to size, charge of the protein at specific pH values, affinity methods, etc., recombinant STH (e.g., the STH-Q isoform or the STH-R isoform) may be extracted from suitable host cells transformed with a vector capable of expressing nucleic acid encoding STH (e.g., the STH-Q allele or the STH-R allele).

It is also within the confines of the present invention to provide a transgenic non-human animal whose genome comprises a disruption in the STH gene, or a transgenic non-human animal that overexpresses STH protein (e.g., the STH-Q or STH-R isoform). The STH gene is known to exist in non-human animals, particularly mice. The non-human animal may be any suitable animal (e.g., cat, cattle, dog, horse, goat, rodent, and sheep), but is preferably a rodent. More preferably, the non-human animal is a rat or a mouse. The transgenic non-human animal of the present invention may be produced by a variety of techniques for genetically engineering transgenic animals, including those known in the art.

As used herein, the term "transgenic non-human animal" refers to a genetically-engineered non-human animal, produced by experimental manipulation, whose genome has been altered by introduction of a transgene. As further used herein, the term "transgene" refers to a nucleic acid (e.g., DNA or a gene) that has been introduced into the genome of an animal by experimental manipulation, wherein the introduced gene is not endogenous to the animal, or is a modified or mutated form of a gene that is endogenous to the animal. The modified or mutated form of an endogenous gene may be produced through human intervention (e.g., by introduction of a point mutation, introduction of a frameshift mutation, deletion of a portion or fragment of the endogenous gene, insertion of a selectable marker gene, insertion of a termination codon, etc.). A transgenic non-human animal may be produced by several methods involving human intervention, including, without limitation, introduction of a transgene into an embryonic stem cell, newly fertilized egg, or early embryo of a non-human animal; integration of a transgene into a chromosome of the somatic and/or germ cells of a non-human animal; and any of the methods described herein.

In one embodiment, the transgenic animal of the present invention has a genome in which the STH gene has been selectively inactivated, resulting in a disruption in its endogenous STH gene. As used herein, a "disruption" refers to a mutation (i.e., a permanent, transmissable change in genetic material) in the STH gene that prevents normal expression of functional STH protein (e.g., it results in expression of a mutant STH protein; it prevents expression of a normal amount of STH protein; or it prevents expression of STH protein). Examples of a disruption include, without limitation, a point mutation, introduction of a frameshift mutation, deletion of a portion or fragment of the endogenous gene, insertion of a selectable marker gene, and insertion of a termination codon. As used herein, the term "mutant" is used herein to refer to a gene (or its gene product) which exhibits at least one modification in its sequence (or its functional properties) as compared with the wild-type gene (or its gene product). In contrast, the term "wild-type" refers to the characteristic genotype (or phenotype) for a particular gene (or its gene product), as found most frequently in its natural source (e.g., in a natural population). A wild-type animal, for example, expresses functional STH.

Selective inactivation in the transgenic non-human animal of the present invention may be achieved by a variety of methods, and may result in either a heterozygous disruption (wherein one STH gene allele (e.g., the STH-Q allele or the STH-R allele) is disrupted, such that the resulting transgenic animal is heterozygous for the mutation) or a homozygous disruption (wherein both STH alleles—STH-Q and STH-R—are disrupted, such that the resulting transgenic animal is homozygous for the mutation).

In one embodiment of the present invention, the endogenous STH gene of the transgenic animal is disrupted through homologous recombination with a nucleic acid sequence that encodes a region common to STH gene products. By way of example, the disruption through homologous recombination may generate a knockout mutation in the STH gene, particularly a knockout mutation wherein at least one deletion has been introduced into at least one exon of the STH gene. Additionally, a disruption in the STH gene may result from insertion of a heterologous selectable marker gene into the endogenous STH gene.

The method for creating a transgenic non-human animal having a knockout mutation in its STH gene may comprise the following steps: (a) generating an STH targeting vector; (b) introducing the STH targeting vector into a recipient cell of a non-human animal, to produce a treated recipient cell; (c) introducing the treated recipient cell into a blastocyst of a non-human animal, to produce a treated blastocyst; (d) introducing the treated blastocyst into a pseudopregnant non-human animal; (e) allowing the transplanted blastocyst to develop to term; (f) identifying a transgenic non-human animal whose genome comprises a knockout disruption in its endogenous STH gene; and (g) breeding the transgenic non-human animal to obtain a transgenic non-human animal exhibiting decreased expression of STH protein relative to wild-type.

It is also within the confines of the present invention to provide a transgenic non-human animal that overexpresses STH (e.g., the STH-Q isoform or the STH-R isoform). The non-human animal may be any suitable animal (e.g., cat, cattle, dog, horse, goat, rodent, and sheep), but is preferably a rodent. More preferably, the non-human animal is a rat or a mouse. The transgenic non-human animal of the present invention may be produced a variety of techniques for genetically engineering transgenic animals, including those known in the art. For example, the transgenic animal may be produced by several methods involving human intervention, including, without limitation, introduction of a transgene into an embryonic stem cell, newly fertilized egg, or early embryo of a non-human animal; integration of a transgene into a chromosome of the somatic and/or germ cells of a non-human animal; and any of the methods described herein.

After the transgenic animals of the present invention (i.e., a transgenic non-human animal whose genome comprises a disruption in the STH gene and a transgenic non-human animal that overexpresses STH-Q or STH-R) have been produced, each may be analyzed to determine if the transgene resulted in a pathology (e.g., the accumulation of neuritic plaques or neurofibrillary tangles). If pathologies do not develop in the animals, the transgenic animals may be crossed with other transgenic animals that do develop pathologies (e.g., the accumulation of neuritic plaques or neurofibrillary tangles), to determine whether the presence of the transgene accelerates the pathology in question. For example, the inventors believe that the STH-R isoform of STH protein may be responsible for accelerating such pathologies as neuritic plaques and neurofibrillary tangles.

The present invention also provides a method for determining whether a subject has or had a neurodegenerative disease (in the case of autopsy), or is at increased risk for developing a neurodegenerative disease. As used herein, the "subject" is a mammal (either living or deceased), including, without limitation, a cow, dog, human, monkey, mouse, pig, or rat, but is preferably a human. Examples of neurodegenerative diseases include, without limitation, Alzheimer's disease, amyotrophic lateral sclerosis (Lou Gehrig's Disease), Binswanger's disease, corticobasal degeneration (CBD), dementia lacking distinctive histopathology (DLDH), frontotemporal dementia (FTD), Huntington's chorea, multiple sclerosis, myasthenia gravis, Parkinson's disease, Pick's disease, and progressive supranuclear palsy (PSP). In the method of the present invention, the neurodegenerative disease is preferably Alzheimer's disease (AD).

As disclosed herein, the STH-R genotype is associated with an increased risk of developing Alzheimer's disease. The homozygous STH-R genotype is associated with the highest probability of developing AD. Therefore, detection of the presence of the STH-R allele in a diagnostic sample of a subject is indicative that the subject has a neurodegenerative disease (e.g., AD), or had a neurodegenerative disease (e.g., AD) (in the case of autopsy), or is at increased risk for developing a neurodegenerative disease (e.g., AD).

Accordingly, the method of the present invention comprises assaying a diagnostic sample of the subject for the presence of one or more alleles of the saitohin (STH) gene, wherein detection of the presence of the STH-R allele is indicative that the subject has a neurodegenerative disease (e.g., AD), or had a neurodegenerative disease (e.g., AD) (in the case of autopsy), or is at increased risk for developing a neurodegenerative disease (e.g., AD). As used herein, the term "at increased risk for developing a neurodegenerative disease" refers to a subject who is/was predisposed to a neurodegenerative disease, has/had a genetic susceptibility for a neurodegenerative disease, or is/was more likely to develop a neurodegenerative disease than a subject in whom the STH-R allele of the STH gene is not present (i.e., a subject homozygous for STH-Q). In a preferred embodiment of the present invention, the method described herein is used to determine whether a subject has AD or had AD (in the case of autopsy), or is at increased risk for developing AD, and detection of the presence of the STH-R allele is indicative that the subject has AD (or had AD) or is at increased risk for developing AD. In one embodiment, the AD is late-onset AD (LOAD).

Screening for the presence of STH-R in a diagnostic sample of a subject offers a non-invasive method for determining whether a subject has AD or had AD (in the case of autopsy), or is at an increased risk of developing AD. It is contemplated that the method of the present invention may be used alone, or in addition to other screens for AD risk factors (e.g., ApoE4) (see, e.g., U.S. Pat. Nos. 5,716,828; 5,767,248; and 6,136,530).

According to the method of the present invention, the diagnostic sample of a subject may be assayed in vitro or in vivo. In accordance with the present invention, where the assay is performed in vitro, a diagnostic sample from the subject may be removed using standard procedures. The diagnostic sample may be tissue, particularly any brain tissue, kidney tissue, muscle tissue, nervous tissue, retinal tissue, or soft tissue, which may be removed by standard biopsy. In addition, the diagnostic sample may be a bodily fluid, including blood, cerebrospinal fluid, pericardial fluid, peritoneal fluid, saliva, serum, and urine. In a preferred embodiment, the diagnostic sample is blood. The diagnostic sample may be taken, for example, from a subject or patient suspected of having a neurodegenerative disease (e.g., AD), a subject or patient not known to have a neurodegenerative disease (e.g., AD), a subject or patient whose family has a history of neurodegenerative disease (e.g., AD), a subject or patient who exhibits cognitive decline, and elderly subjects or patients.

In the method of the present invention, the diagnostic sample of a subject may be assayed for the presence of one or more alleles of the STH gene (e.g., the STH-Q allele or the STH-R allele) using assays and detection methods readily determined from the known art, including, without limitation, immunological techniques, hybridization analysis of nucleic acid (e.g., genomic DNA) extracted from the diagnostic sample taken from the subject, fluorescence imaging techniques, radiation detection, polymerase chain reaction (PCR), ligase chain reaction (LCR), RIA assay, and ELISA assay.

Nucleic acid may be isolated from a diagnostic sample of a subject using standard techniques known to one of skill in the art. Isolated nucleic acid may be amplified by procedures known in the art, including, without limitation, ligase chain reaction (LCR) (21) and polymerase chain reaction (PCR) (see, e.g., U.S. Pat. Nos. 4,683,195; 4,683,202; 4,800,159; and 4,965,188). For example, in the method of the present invention, genomic DNA encoding part or all of the STH gene may be isolated from a diagnostic sample of a subject, and amplified using at least one pair of STH-specific or STH-region-specific oligonucleotide primers, such as those disclosed herein. The amplified DNA that is thereby generated then may be incubated with a restriction enzyme, including any disclosed herein, that is capable of cleaving DNA at sites specific to the STH region to form a digest. Thereafter, the size of the DNA fragments in the digest may be determined. The presence of a DNA fragment having a size that differs from the size of a DNA fragment in a control sample lacking the STH-R allele indicates the presence of the STH-R allele in the diagnostic sample of the subject.

According to this method of the present invention, the hybridization analysis may be conducted using Northern blot analysis of mRNA. Additionally, this method of the present invention may be conducted by performing a Southern blot analysis of DNA using one or more nucleic acid probes that hybridize to nucleic acid encoding STH (e.g., the STH-Q allele or the STH-R allele). The nucleic acid probes may be prepared by a variety of techniques known to those skilled in the art, including, without limitation, the following: restriction enzyme digestion of nucleic acid encoding STH protein; automated synthesis of oligonucleotides having sequences which correspond to selected portions of the nucleotide sequence of the STH gene, using commercially-available oligonucleotide synthesizers, such as the Applied Biosystems Model 392 DNA/RNA synthesizer; and any methods disclosed herein.

The STH nucleic acid used in the probes may be derived from mammalian, preferably human, STH. The nucleic acid probes used in the method of the present invention may be DNA or RNA, and may vary in length from about 8 nucleotides to the entire length of the STH nucleic acid. In addition, the probes may be prepared in accordance with probe preparation methods described above. Furthermore, the nucleic acid probes of the present invention may be labeled with one or more detectable markers. Labeling of the nucleic acid probes may be accomplished using one of a number of methods known in the art, including those described above, along with one of a variety of labels, including those described above. Combinations of two or more nucleic acid probes (or primers), corresponding to different or overlapping regions of the STH nucleic acid, also may be used to assay a diagnostic sample for STH expression, using, for example, PCR or RT-PCR.

As disclosed herein, the presence of the STH-R isoform of the STH appears to increase the risk of developing AD. Thus, genotyping is also possible by direct examination of the STH protein present in either the tissue or bodily fluid of a subject. Accordingly, in the method of the present invention, the diagnostic sample of a subject also may be assayed for the presence of one or more alleles of the STH gene by assaying for expression of one or more isoforms of the STH protein (e.g., the STH-Q isoform and the STH-R isoform). As used herein, "expression" means the transcription of the STH gene into at least one mRNA transcript, or the translation of at least one mRNA into an STH protein, as defined above. Accordingly, a diagnostic sample may be assayed for STH expression by assaying for STH protein (as defined above), STH cDNA, or STH mRNA. The appropriate form of STH will be apparent based on the particular techniques discussed herein.

Protein may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (with an antibody specific to STH), and precipitation (e.g., with isopropanol and a reagent such as Trizol). Isolation and purification of the protein may be followed by electrophoresis (e.g., on an SDS-polyacrylamide gel).

In accordance with the method of the present invention, a diagnostic sample of a subject may be assayed for STH expression, and STH expression may be detected in a diagnostic sample, using assays and detection methods readily determined from the known art, including, without limitation, immunological techniques, hybridization analysis, fluorescence imaging techniques, radiation detection, PCR, LCR, RIA assay, and ELISA assay. For example, according to the method of the present invention, a diagnostic sample of the subject may be assayed for STH expression using an agent reactive with STH. As used herein, "reactive" means the agent has affinity for, binds to, or is directed against STH. As further used herein, an "agent" shall include a protein, polypeptide, peptide, nucleic acid (including DNA or RNA), antibody, Fab fragment, $F(ab')_2$ fragment, molecule, compound, antibiotic, drug, any of the agents disclosed above, and any combinations thereof. Preferably, the agent of the present invention is labeled with a detectable marker.

In one embodiment of the present invention, the agent reactive with STH is an allele-specific antibody (e.g., specific for the STH-Q allele or specific for the STH-R allele). As used herein, the antibody of the present invention may be polyclonal or monoclonal. In addition, the antibody of the present invention may be produced by techniques well known to those skilled in the art, including any of those described above. The antibodies used herein may be labeled with a detectable marker. Labeling of an antibody may be accomplished using one of a variety of labeling techniques, including those known in the art and those described above. The detectable marker of the present invention may be any of those known in the art, as well as any above-described detectable markers. Preferably, the agent of the present invention is a high-affinity antibody labeled with a detectable marker.

Where the agent of the present invention is an antibody reactive with STH, a diagnostic sample taken from the subject may be purified by passage through an affinity column which contains STH antibody as a ligand attached to a solid support such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The STH antibody may be further attached to the solid support through a spacer molecule, if desired. Appropriate binding conditions (e.g., temperature, pH, and salt concentration) may be readily determined by the skilled artisan. In one embodiment, the STH antibody is attached to a sepharose column, such as Sepharose 4B.

Where the agent is an antibody, a diagnostic sample of the subject may be assayed for STH expression using binding studies that utilize one or more antibodies immunoreactive with STH, along with standard immunological detection techniques. For example, the STH protein eluted from the affinity column may be subjected to an ELISA assay, an RIA assay, Western blot analysis, flow cytometry, or any other immunostaining method employing an antigen-antibody interaction. In a preferred embodiment of the present invention, the diagnostic sample is assayed for STH expression using an ELISA assay.

In accordance with the method of the present invention, the detection of the presence of one or more alleles of STH in a diagnostic sample of a subject may be followed by an assay to measure or quantify the relative and total amounts of STH-Q and STH-R present in the diagnostic sample of the subject. Such assays are well known to one of skill in the art, and may include immunohistochemistry/immunocytochemistry, flow cytometry, mass spectroscopy, Western blot analysis, or an ELISA for measuring amounts of STH protein. For example, to use an immunohistochemistry assay, histological (paraffin-embedded) sections of tissue may be placed on slides, and then incubated with an antibody against STH. The slides then may be incubated with a second antibody (against the primary antibody), which is tagged to a dye or other calorimetric system (e.g., a fluorochrome, a radioactive agent, or an agent having high electron-scanning capacity), to permit visualization of STH present in the sections.

It is contemplated that the diagnostic sample in the present invention frequently will be assayed for STH expression not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for the presence of one or more alleles of STH.

As disclosed herein, two known alleles of the STH gene (STH-Q and STH-R) are present in the human population. Therefore, there are three possible genotypes: (1) homozygous for STH-Q, or QQ; (2) homozygous for STH-R, or RR; and (3) heterozygous, having one copy of STH-Q and one copy of STH-R, abbreviated QR. The inventors have found that a correlation exists between the presence of the STH-R genotype in a subject, and the subject's risk of developing Alzheimer's disease. In particular, the presence of a single STH-R allele (i.e., the subject is heterozygous for STH-R, or QR) is associated with an increased risk of developing AD, while the presence of two STH-R alleles (i.e., the subject is homozygous for STH-R, or RR) is associated with the highest risk of developing AD.

In view of the foregoing, it is also contemplated in the present invention that assaying a diagnostic sample of a subject for the presence of one or more alleles of STH may be a useful means of providing information concerning the prognosis of a subject or patient who has, or may develop, a neurodegenerative disease (e.g., AD). Accordingly, the present invention further provides a method for assessing the prognosis of a subject who has a neurodegenerative disease, or who may develop a neurodegenerative disease, comprising assaying a diagnostic sample of the subject for the presence of one or more alleles of STH, wherein the presence of two STH-R alleles in the diagnostic sample of the subject indicates a more negative prognosis for the subject.

In accordance with the method of the present invention, the neurodegenerative disease may be any of those described above, including Alzheimer's disease (AD). In a preferred embodiment, the neurodegenerative disease is AD. In one such preferred embodiment, the AD is late-onset AD (LOAD). The diagnostic sample of the subject may be a tissue or a bodily fluid, as described above, and may be removed from the subject by known procedures, including those discussed above. In one embodiment, the diagnostic sample is a blood sample. Additionally, the diagnostic sample may be assayed either in vitro or in vivo, using all of the various assays, detection methods, and quantification methods described above. Furthermore, the diagnostic sample of a subject or patient may be assayed, and the presence of one or more alleles of STH may be determined, at any time before, during, or following the determination that the subject or patient has a neurodegenerative disease (e.g., AD), or is at increased risk of developing a neurodegenerative disease (e.g., AD).

It is contemplated that the diagnostic sample of the present invention frequently will be assayed for the presence of one or more alleles of STH not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for the presence of one or more alleles of STH.

The inventors' biochemical results have shown that the STH-R isoform of the STH protein accumulates in the brain to a greater extent than does the STH-Q isoform. Therefore, detection of increased levels of STH appears to be indicative of the presence of the STH-R genotype. Since the STH-R isoform of the STH protein accumulates in the brain and possibly other tissues, it is reasonable to expect that this accumulation will be reflected by increased levels in the cerebrospinal fluid and blood. Accordingly, detection of increased risk of development of AD may simply require only the measurement of levels of STH protein in a diagnostic sample of a subject. Elevated levels of STH protein then would be indicative of the presence of at least one copy of the STH-R allele sequence in the subject.

In view of the foregoing, it is also within the confines of the present invention to provide a method for determining whether a subject has Alzheimer's disease (AD) or had AD (in the case of autopsy), or is at increased risk for developing AD, comprising assaying a diagnostic sample of the subject for expression of STH protein, wherein detection of STH expression elevated above normal is indicative that the subject has AD (or had AD, in the case of autopsy), or is at increased risk for developing AD.

As used herein, "STH expression elevated above normal" means expression of STH at a level that is significantly greater than the level expected for the same type of diagnostic sample taken from a nondiseased subject or patient (i.e., one who does not have a neurodegenerative disease (e.g., AD) or a detectable increased risk of developing a neurodegenerative disease (e.g., AD)) of the same gender and of similar age. As further used herein, "significantly greater" means that the difference between the level of STH expression that is elevated above normal, and the expected (normal) level of STH, is of statistical significance. Preferably, STH expression elevated above normal is expression of STH at a level that is at least 10% greater than the level of STH expression otherwise expected. Where STH expression is expected to be absent from a particular diagnostic sample taken from a particular subject or patient, the normal level of STH expression for that subject or patient is nil. Where a particular diagnostic sample taken from a particular subject or patient is expected to have a low level of constitutive STH expression, that low level is the normal level of STH expression for that subject or patient.

Expected or normal levels of STH expression for a particular diagnostic sample taken from a subject or patient may be easily determined by assaying nondiseased subjects of a similar age and of the same gender. Once the appropriate samples have been obtained, the normal quantities of STH expression in men and women may be determined using a standard assay for quantification, such as flow cytometry, Western blot analysis, or an ELISA for measuring protein quantities, as described below. For example, an ELISA may be run on each sample in duplicate, and the means and standard deviations of the quantity of the STH protein may be determined. If necessary, additional subjects may be recruited before the normal quantities of STH expression are quantified.

In accordance with the method of the present invention, the neurodegenerative disease may be any of those described above, including Alzheimer's disease (AD). In a preferred embodiment, the neurodegenerative disease is AD. In one such preferred embodiment, the AD is late-onset AD (LOAD). The diagnostic sample of the subject may be a tissue or a bodily fluid, as described above, and may be removed from the subject by known procedures, including those discussed above. In one embodiment, the diagnostic sample is a blood sample. Additionally, the diagnostic sample may be assayed either in vitro or in vivo, using all of the various protein assays, protein detection methods, and protein quantification methods described above (e.g., by ELISA and RIA). In one embodiment, the diagnostic sample is assayed using an agent reactive with STH, as defined above. The agent may be labeled with a detectable marker, as described above. In a preferred embodiment, the diagnostic sample is assayed using an antibody that selectively binds STH. Preferably, the antibody is labeled with a detectable marker.

Since increased levels of STH protein appear to be associated with an increased risk of Alzheimer's disease, overexpression of this protein in either cells in culture or in rodents (by transgenic means) will provide valuable insights into mechanisms by which overexpression of STH protein increases risk for Alzheimer's disease. Mice or cell cultures expressing the STH-R isoform of STH (including the above-described transgenic nonhuman animals and transformed host cells) will be especially valuable in this regard. The STH-R homozygotes in the human population have demonstrated that the RR genotype is sufficient to cause Alzheimer's disease, even in the absence of other risk factors for Alzheimer's, such as an ApoE4 allele. Thus, mice overexpressing the STH-R isoform of STH can be expected to develop an Alzheimer's-disease—like condition. Such mice will be extremely valuable in the development and testing of therapies for this disease.

The discovery that there is a correlation between the presence of the STH-R genotype in a subject, and the subject's risk of developing Alzheimer's disease, provides a means of identifying patients who have AD or another neurodegenerative disease, or who are at increased risk of developing AD or another neurodegenerative disease, and presents the potential for commercial application in the form of a test to screen for susceptibility to the development of a neurodegenerative disease, such as AD. The development of such a test could provide general screening procedures that may assist in the early detection and diagnosis of neurodegenerative diseases, such as AD, and/or provide a method for the follow-up of patients who have been diagnosed with a neurodegenerative disease (e.g., AD) or identified as being at increased risk of developing a neurodegenerative disease (e.g., AD).

Accordingly, the present invention further provides a kit for use as a screening assay to identify a subject who has a neurodegenerative disease (e.g., AD), or who is at increased risk of developing a neurodegenerative disease (e.g., AD). The kit of the present invention comprises at least one reagent for use in an assay to detect directly the presence of a nucleic acid sequence encoding one or more alleles of STH, or at least one reagent for use in an assay to detect the presence of one or more isoforms of STH protein. The kit also comprises instructions for using the kit to determine whether the subject has Alzheimer's disease (AD) or had AD (in the case of autopsy), or is at increased risk for developing AD.

Such instructions, for example, may provide that the kit may be used to assay a diagnostic sample of a subject for the presence of one or more alleles of saitohin (STH), wherein detection of the presence of the STH-R allele is indicative that the subject has AD (or had AD, in the case of autopsy), or is at increased risk for developing AD. Additionally, such instructions also may provide that the kit may be used to assay a diagnostic sample of a subject for expression of saitohin (STH) protein, wherein detection of STH expression elevated above normal is indicative that the subject has AD (or had AD), or is at increased risk for developing AD. In one embodiment of the present invention, the kit further comprises a container in which the reagent and the instructions are packaged.

A kit designed to detect the presence of a nucleic acid sequence encoding one or more alleles of STH may contain an agent specifically reactive with STH. The agent may be any of those described above, including oligonucleotide probes that selectively bind to a nucleic acid sequence encoding the STH-Q allele or the STH-R allele of the STH gene, and may be used in any of the above-described assays or methods for detecting or quantifying the presence of one or more alleles of STH. The kit of the present invention also may include allele-specific probes that can hybridize to amplified fragments of a nucleic acid sequence corresponding to part or all of the STH gene, and that can be used to identify the presence of one or more alleles of STH. Furthermore, a kit designed to detect the presence of a nucleic acid sequence encoding one or more alleles of STH may contain primers that hybridize to a nucleic acid sequence corresponding to part or all of the STH gene, and that permit the amplification of said sequence (e.g., by LCR, PCR, and other amplification procedures known in the art).

A kit designed to detect the presence of one or more isoforms of the STH protein may contain an agent specifically reactive with STH. The agent may be any of those described above, including an allele-specific antibody that selectively binds the STH-Q or the STH-R isoform of the STH protein, and may be used in any of the above-described assays or methods for detecting or quantifying the presence of one or more alleles of STH. The kit of the present invention also may include at least one allele-specific antibody directed to STH, preferably labeled with a detectable marker, along with a solid support capable of binding STH protein.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Introduction

In February, the Human Genome Project completed the sequencing for the genomic clones overlapping the tau locus on Chromosome 17q21, and an expressed sequence tag (EST) (accession #AA325304) was identified in a tau intron approximately 2.5 kb downstream of exon 9 of the tau gene that is shown in FIG. 6. This location was of particular interest to the inventors, because most of the mutations in FTD are in or around this intron and adjacent exons of tau (3). The EST was found to be expressed in the Marathon cerebellar cDNA library (Clontech), and in a human oligodendroglioma cell line (that expresses tau). However, mRRNlA isolated from COS7 cells failed to yield an RT-PCR product, thereby suggesting that the mRNA was not expressed in COS7 cells (data not shown).

Using RNA from a human oligodendroglioma cell line, the inventors discovered a new human gene, which exists in at least two forms in the human population. This gene, which they have named saitohin (STH), is on chromosome 17, within an intron of the gene encoding the microtubule-associated protein tau. The protein encoded by the saitohin gene is not similar to the microtubule-associated protein tau, nor is it substantially similar to any other known protein. Furthermore, searches of the protein data base have not revealed another protein with significant homology to saitohin.

2. Materials and Methods

A. Cloning of Saitohin (STH) Gene

Using RNA from a human oligodendroglioma cell line, the 5' and 3' ends of the putative gene were cloned with the Gene Racer kit (Invitrogen). The sequence of the full-length clones revealed a new gene, saitohin (STH) [named in honor of late Dr. Tsunao Saitoh and his lab], which was intron-less and in the sense direction relative to tau.

B. Analysis of STH Gene Expression

Figure 8C:
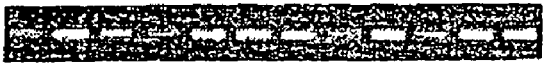
FIG. 8 shows the human expression of saitohin and tau in multiple tissues and the central nervous system. RT-PCR was performed on the Human Tissue Rapid-Scan™ Panel (Origene) (panels A and B) and the Human Brain Rapid-Scan™ Panel (Origene) (panels C and D) according to published protocols (11). Saitohin expression is shown in the panels as a single band (panels A and C). In panels B and D, the expression of the tau isoforms is represented by two bands. The upper band consists of isoforms with exon 10, and the lower band contains the isoforms without exon 10. The lanes of multiple tissues in panels A and B are as follows: 1—brain; 2—heart; 3—kidney; 4—spleen; 5—liver; 6—colon; 7—lung; 8—small intestine; 9—muscle; 10—stomach; 11—testis; 12—placenta; 13—salivary gland; 14—thyroid; 15—adrenal; 16—pancreas; 17—ovary; 18—uterus; 19—prostate; 20—skin; 21—PBL; 22—bone marrow; 23—fetal brain; and 24—fetal liver. The lanes for (panels C and D) are as follows: 1—frontal lobe; 2—temporal lobe; 3—cerebellum; 4—hippocampus; 5—substantia nigra; 6—caudate nucleus; 7—amygdala; 8—thalamus; 9—hypothalamus; 10—pons; 11—medulla; and 12—spinal cord.
Figure 8D:
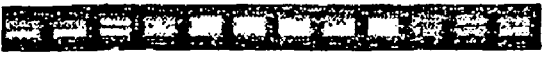

To further characterize STH, the inventors analyzed the gene expression in 24 human tissues, using the Human Tissue Rapid-Scan$^a$ Panel (Origene) (FIG. 8). Since STH and tau share a common genetic locus, the inventors hypothesized that STH and tau could be coordinately expressed. Therefore, the expression of tau was also examined. To determine whether the location of STH upstream of the alternatively spliced exon 10 would affect its expression, the tau isoforms with exon 10 (FIG. 8, panel A, upper band) and without exon 10 (FIG. 8, panel A, lower band) were also examined. Because tau and STH have a significant overlap in general tissue expression, an expanded study was performed using the Human Brain Rapid-Scan$^a$ Panel (Origene) to determine the central nervous system (CNS) expression patterns, and to ascertain whether STH and tau are coordinately expressed in the brain.

In these studies, cDNA was amplified using the "Touchdown" PCR method (11). The primers used were F Cel I (5'-ccc tgt aaa ctc tga cca cac-3') (SEQ ID NO:5) and R Gel I (5'-cat ggg aag tag ctt ccc tgt-3') (SEQ ID NO:6). PCR was performed in a 50-μl reaction mixture containing 20 mM Tris-HCl (pH 8.4), 50 mM KCl, 1.5 mM $MgCl_2$, 0.2 μM of each primer, 0.2 mM dNTPs, 2 μl of genomic DNA, and 1 U of Taq polymerase (Invitrogen).

The touchdown PCR method for saitohin consists of the following steps: An incubation at 94° C. for 3 mm is followed by a step of 94° C. for 30 sec, a step of 65° C. for 30 sec for the initial annealing cycle (in each subsequent cycle, the annealing temperature is decreased by 0.2° C.), and a step of 72° C. for 30 sec for polymerization. This sequence is then repeated for 25 cycles. Finally, an additional set of 10 cycles is performed, consisting of 94° C. for 30 sec, 60° C. for 30 sec, and 72° C. for 30 sec. The last cycle is followed by an incubation at 72° C. for 30 sec. For the amplification of tau transcripts, the PCR cocktail and touchdown program were the same as above, except the tau sense primer was a 21-mer 5'-gcc aac gcc acc agg att cca gca aaa-3' (SEQ ID NO:7), the antisense pnmer was a 21-mer 5'-ttt act tcc acc tgg cca cct-3' (SEQ ID NO:8), and a longer PCR polymerization time of 55 sec was used. Both saitohin and tau PCR products were run on a 2.0% agarose gel with ethidium bromide.

C. PCR Amplification and Restriction-Enzyme Digestion of STH DNA

For the alleleotyping gel (FIG. 5), HinFI-digested PCR products of the genotypes QQ, QR, and RR were prepared in accordance with known protocols. In particular, the genomic DNA of the subjects was extracted from frozen brain tissue using a genomic-DNA extraction kit, according to manufacturer protocols (Qiagen). The saitohin DNA sequence then was amplified from genomic DNA from AD and normal control subjects using the above PCR protocol for saitohin, using the primers F-Cel I and R-Cel I. Sequencing of the PCR products identified a nucleotide polymorphism A->G, changing the amino acid at position 7 from a glutamine (Q) to an arginine (R), thereby creating a new HinFI restriction enzyme site. For genotyping, the PCR products were digested with 5 units of HinFI {5'-GANTC-3'} restriction enzyme (New England Biolabs), for 3 h at 37° C., then run on a 2.0% agarose gel with ethidium bromide.

D. STH Monoclonal Antibodies

Figure 9:
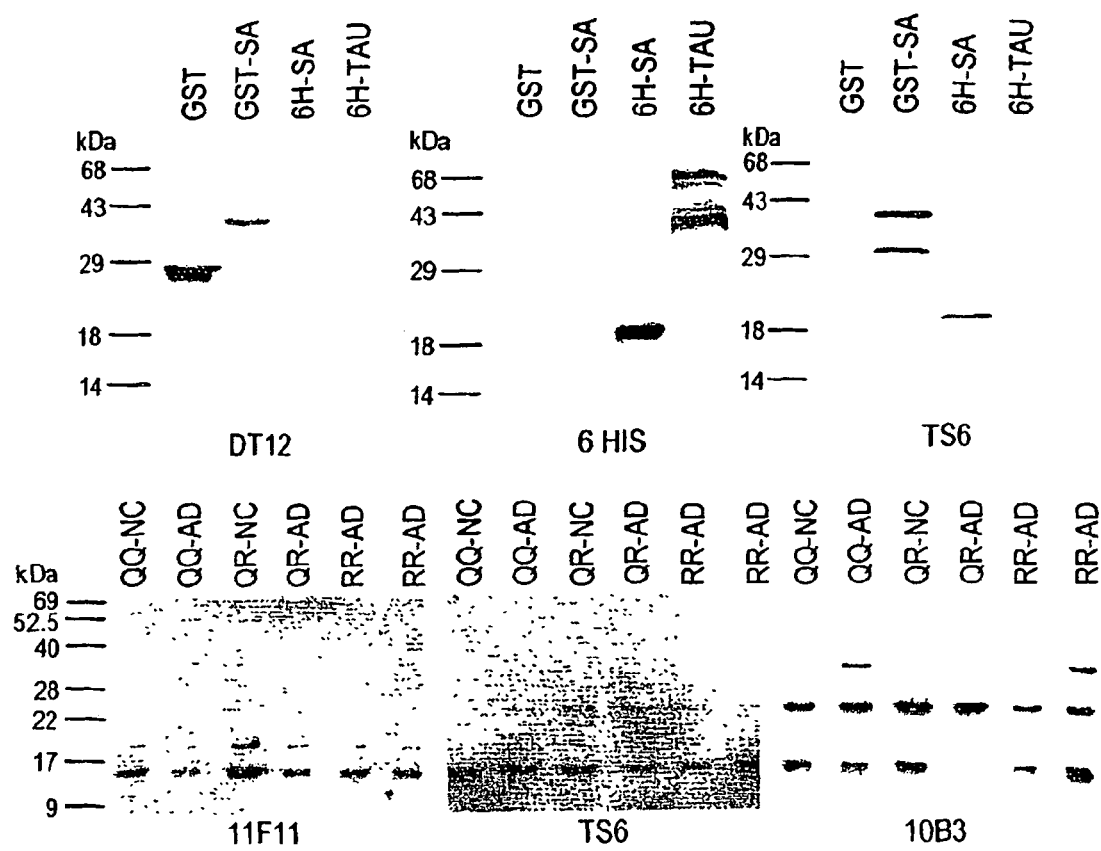
FIG. 9 sets forth a Western blot analysis of normal (NC) and Alzheimer's disease (AD) subjects with the QQ, QR, and RR genotypes. The top three panels show immunoblots of whole lysates of IPTG-induced bacteria expressing recombinant 6XHis-tagged saitohin (6H-SA), or 6XHis-tagged tau (6H-TAU), or glutathione S-transferase (GST), or GST-saitohin fusion protein (GST-SA), with antibodies to GST (DT12), 6XHIS (6 HIS), and saitohin (TS6). The bottom three panels are immunoblots of partially purified brain homogenates from QQ, QR, or RR genotypes of AD (QQ-AD, AD-QR, and AD-RR) and normal (QQ-NC, QR-NC) subjects, with left, center, and right panels of STH monoclonal antibodies (11F11, TS6, and 10B3, respectively), according to published protocols (12).

Saitohin monoclonal antibodies 11F11 (IgG2B), TS6 (IgM), and 10B3 (IgM) were generated as previously described (12) by immunizing mice with both recombinant and synthetic peptides of STH. Brain protein samples of normal (NC) and Alzheimer's disease (AD) subjects with the QQ, QR, and RR genotypes were homogenized in 1XBS (2 mM PMSF), and protein was partially purified by size fractionation. Subsequently, the prepared samples were incubated in a urea sample buffer for 30 min at 37° C., and then were run on a 15% SDS-PAGE gel (FIG. 9). ECL-Western blot analysis was performed using previously described protocols (12).

3. Results and Discussion

Nucleotide and amino acid sequence analyses of the STH gene (FIG. 7) revealed that STH encodes a 128-amino-acid protein that appears to have no clear homology to genes, proteins, signal sequences, or motifs (14). However, the location of STH within the tau locus could provide insight into its function. Since both STH and tau share a similar expression pattern, tau and STH could function together as in the example of the choline acetyltransferase\ vesicular acetylcholine transporter gene locus (15). The mouse genome contains a sequence which is 100% identical to the saitohin open reading frame, strongly suggesting that this gene is conserved between rodents and humans. The mouse genome contains a sequence that is 100% identical to the STH open reading frame, strongly suggesting that this gene is conserved between rodents and humans.

To further characterize STH, the inventors analyzed gene expression in 24 human tissues, using the Human Tissue Rapid-Scan$^a$ Panel (Origene). The expression of STH was highest in placenta, muscle, fetal brain and adult brain, with low expression in heart, kidney, stomach, testis, and adrenal gland (FIG. 8, panel A). Since STH and tau share a common genetic locus, they could be coordinately expressed; therefore, the expression of tau was also determined. To determine whether the location of STH upstream of the alternatively spliced exon 10 would affect its expression, the tau isoforms with exon 10 and without exon 10 were also examined. As shown in FIG. 8, panel B, the expression of tau was found to be highest in heart, kidney, muscle, testis, salivary glands, adrenal glands, adult and fetal brain with low expression in placenta, thyroid, prostate, and skin. This is in agreement with other reports of tau expression (16).

Because tau and STH have a significant overlap in general tissue expression, an expanded study was performed using the Human Brain Rapid-Scan$^a$ Panel (Origene) to determine the central nervous system (CNS) expression patterns, and to ascertain whether STH and tau are coordinately expressed in the brain. FIG. 8, panel C, shows that STH is expressed in the CNS, with higher expression in the temporal lobe, hypothalamus, medulla, and spinal cord, and with lower expression in the other brain regions. As depicted in FIG. 8, panel D, the expression of tau is high in most of the CNS samples, except in the pons, where the expression is lower.

Based upon the general tissue and CNS tissue expressions analyzed by the inventors, it appears that tau shares some tissue expression with STH; however, there are some differences. Taken together, the results indicate that STH is not under the regulation of the tau promoter, but could share some regional regulatory elements with the tau gene, which could have implications for the function of STH. The location and expression of STH upstream of the exon 10 does not appear to correlate with the splicing of exon 10 of tau in the CNS or the other tissues.

The location of STH warrants investigation into its possible role in neurodegenerative disorders, since there is genetic evidence implicating the tau locus in many of these diseases. During the sequencing of the STH gene from human subjects, a nucleotide polymorphism (A->G) was identified that changes a glutamine (Q) to arginine (R) at amino acid position 7 (Q7R) of STH, as shown in FIG. 7. The "G" polymorphism (R allele) creates a novel HinfI restriction enzyme site that generates a distinctive fragment pattern as compared to the "A" nucleotide (Q allele). A representative gel is shown in FIG. 5.

The distribution of AD and normal control subjects with different STH alleles and frequencies were tabulated in Table 1. The two groups of subjects were age-matched, and were limited to Caucasian subjects. The RR genotype was found at a significantly higher frequency in the AD group (16%), as compared to the normal control subjects (0%) (p=0.0232; odds ratio 11.920, by Fisher's Exact Test). The R allele does occur in normal subjects at a frequency of 13%, but at a significantly lower percentage compared to AD subjects in which the R allele is 32% (p=0.0085; odds ratio 3.109, by Fisher's Exact Test). The average age of onset for the RR subjects is 83.1 with a range of 77-93, which provides evidence that RR genotype is a risk factor for late onset Alzheimer's disease.

TABLE 1

STH polymorphism in AD and normal subjects.

| Saitohin Genotype | AD n = 1 | Normal n = 30 |
|---|---|---|
| QQ | 26 (51%) | 22 (73%) |
| QR | 17 (33%) | 8 (27%) |
| RR | 8 (16%) | 0 (0%) |
| Saitohin Alleles | n = 102 | n = 60 |
| Q | 69 (65.6%) | 52 (86.7%) |
| R | 33 (32.4%) | 8 (13.3%) |

A total of 81 subjects were used for the case-control study. The AD group (n = 51) and the normal control group (n = 30) of subjects were autopsy-confirmed and age-matched. The Fisher's Exact Test was used for the comparisons of the allele and genotype frequencies for the groups included.
Normal (average age = 78.83; range 55-97);
Alzheimer's disease (AD) (average age = 80.51; range 56-98)

In addition to the STH genotype, the ApoE genotype of the subjects was also determined, because allele 4 of the ApoE gene is an important risk factor for AD, and because the inventors wanted to investigate whether the ApoE allele 4 could synergize with the STH genotype (17). The ApoE genotypes were in close agreement with the frequencies in the general population, thereby providing evidence against sampling bias (data not shown) (18). In agreement with previous reports, the ApoE4 allele was found to be overrepresented in the inventors' AD group, as compared to normal control subjects shown in Table 2; however, the ApoE alleles were evenly distributed among the RR, QR, and QQ subjects of the AD group in Table 3, suggesting that there is no association between the ApoE and STH genotypes (18).

TABLE 2

ApoE genetics in AD and normal controls.

| ApoE Genotype | AD n = 1 | Normal n = 30 |
|---|---|---|
| 2/2 | 0 (0%) | 0 (0%) |
| 2/3 | 3 (5.9%) | 7 (23.3%) |
| 2/4 | 0 (0%) | 0 (0%) |
| 3/3 | 22 (43.1%) | 19 (63.4%) |
| 3/4 | 20 (39.2%) | 4 (13.3%) |
| 4/4 | 6 (11.8%) | 0 (0%) |
| ApoE Alleles | n = 102 | n = 60 |
| 2 | 3 (2.9%) | 7 (11.7%) |
| 3 | 67 (65.7%) | 49 (81.7%) |
| 4 | 32 (31.4%) | 4 (6.6%) |

ApoE genotyping was carried out as previously described (20). The Fisher's Exact Test was used for comparisons of the ApoE4 carrier (p = 0.0008; OR = 6.760; CI = 2.062-22.166) and ApoE4 allele frequencies (p = 0.0002; OR = 6.4; CI = 2.136-19.178) for the groups included.

TABLE 3

STH genotype compared with ApoE genotype.

| AD n = 51 STH Genotype | ApoE4 Negative n = 25 | ApoE4 Positive n = 26 |
|---|---|---|
| QQ | 13 | 13 |
| QR | 8 | 9 |
| RR | 4 | 4 |
| Normal n = 30 STH Genotype | ApoE4 Negative n = 26 | ApoE4 Positive n = 4 |
| QQ | 20 | 3 |
| QR | 6 | 1 |
| RR | 0 | 0 |

A logistic regression analysis was performed with the statistical program, SPSS, for the determination of associations of ApoE4 with RR genotype in the AD and normal populations.

In addition to the AD group, a small number of subjects with other neurodegenerative disorders, most of which have tau pathology, were also examined for the polymorphism. These results, which are set forth in Table 4, show some interesting trends, and suggest that the STH-Q/R polymorphism may not be AD specific. For example, one subject with dementia lacking distinctive histopathology had the RR genotype, thereby suggesting that this genotype is not AD specific. Furthermore, it appears that PSP subjects have an overrepresentation of the QQ genotype, while FTD and Pick's disease have a higher percentage of QR genotype, when compared with normal controls. Further investigation of these trends with larger groups of subjects is required to determine their significance.

TABLE 4

Saitohin polymorphism in non-AD neurodegenerative disorders.

| Saitohin Genotype | DLDH n = 7 | PSP n = 6 | FTD n = 4 | CBD n = 4 | PICKS n = 9 | ALS n = 1 |
|---|---|---|---|---|---|---|
| QQ | 4 (57%) | 5 (83%) | 1 (25%) | 1 (100%) | 3 (33%) | 1 (100%) |
| QR | 2 (29%) | 1 (17%) | 3 (75%) | 0 | 6 (67%) | 0 (0%) |
| RR | 1 (14%) | 0 (0%) | 0 (0%) | 0 (0%) | 0 (0%) | 0 (0%) |

The numbers of subjects were too small for statistical analysis. Subjects with dementia lacking distinctive histopathology (DLDH), frontotemporal dementia (FTD), Pick's disease (PICKS), progressive supranuclear palsy (PSP), corticobasal degeneration (CBD), and amyotropic lateral sclerosis (ALS), were studied.

The experiments demonstrating STH expression thus far rely upon the use of PCR, which is so sensitive that it is difficult to be sure that bands result from legitimate mRNA transcripts or come from a trace contamination of DNA. When working with an intron-less gene, where the sequence of the mRNA matches up exactly with the genomic DNA encoding the gene, DNA contamination remains a concern. The consistent failure to find evidence of STH mRNA in COS7 cells and in several tissues of the Multiple Tissue cDNA panel argues against contamination.

The inventors generated monoclonal antibodies to the predicted protein, produced as either a 6-His tagged recombinant protein, or as a glutathione S-transferase fusion protein in bacteria, in order to demonstrate the existence of a STH protein product. Using a combination of synthetic peptides from the STH sequence and a deletion mutant protein, the epitopes recognized by these monoclonal antibodies have been mapped to three different regions of STH: the N-terminus, a central region, and the C-terminus. In FIG. 9 (top three panels), three representative immunoblots, with antibodies to GST (DT12), 6XHis, and STH (TS6), demonstrate the specificity of the monoclonal antibodies.

As depicted in FIG. 9 (bottom three panels), STH protein was detected by immunoblots of brain homogenates from AD subjects and normal subjects, using antibodies to the N-terminus (11F11, an IgG2B), the C-terminus (10B3, an IgM), and an intervening sequence (TS6, an IgM) of STH protein. The immunoblots show a protein with an apparent molecular weight of approximately 20 kD-6 kD more than the calculated size of 13.6 kD. A similar protein is recognized by all three antibodies reactive with three different epitopes of STH. In addition, other N-terminal antibodies to STH show a similar blotting result (data not shown). This size difference could be due to amino acid composition, post-translational modification, and/or aggregation with itself or other proteins. The aggregation hypothesis would explain the presence of the higher molecular weight bands common to all of the blots. Further investigation will determine which hypothesis (or hypotheses) is/are correct.

4. Conclusion

Based upon the experiments and results disclosed herein, several things are known about STH. STH is a nested gene in the tau locus. It has a very similar expression pattern to that of tau, suggesting that these two proteins are expressed jointly, and may function together in a pathway. A well-studied example of such a situation is the choline acetyl-transferase (CHAT)/vesicular acetylcholine transporter (VCHAT) gene locus. The VCHAT gene resides within the intron between exons 1 and 2 of the CHAT gene. The VCHAT and CHAT genes, which are coordinately expressed, are involved in the packaging of the neurotransmitter, acetylcholine (ACH), into vesicles, and in the synthesis of ACH, respectively (15). An attractive hypothesis starts to emerge that STH and tau might not only function together normally, but also may function together in disease states.

A Q7R polymorphism in the STH gene was identified in human subjects, and was found to be overrepresented in the homozygous state in the LOAD population. The RR genotype is suggestive of a loss-of-function mutation, because of its homozygous state in AD patients. It is presumed that STH has a normal cellular function. Although sequence analysis has yielded no clues, there may be hints to the function of STH and possible role in AD. Since STH lacks a consensus targeting signal sequence, it is a putative cytosolic protein; thus, it may be placed in the same compartment as tau. STH has no proline-directed phosphorylation sites, unlike tau. However, there are putative phosphorylation sites on STH for PKC and CKII-kinases that normally have significant roles in the central nervous system and are implicated in tau phosphorylation and AD (19). Follow-up genetic studies of STH in neurodegenerative diseases with a variety of tau or amyloid pathologies could help to determine whether STH plays a role in the formation of neurofibrillary tangles and/or amyloid plaques.

REFERENCES

1. Beers and Berkow, eds., *The Merck Manual of Diagnosis and Therapy*, 17$^{th}$ ed. (Whitehouse Station, N.J.: Merck Research Laboratories, 1999) 1395-1398, 1442-48.
2. Myers and Goate, *Curr. Opin. Neurol.*, 14:433, 2001.
3. Buee et al., *Brain Res. Rev.*, 33:95, 2000.
4. Lewis et al., *Science*, 293:1487, 2001.
5. Roks et al., *Neurosci. Lett.*, 277:137, 1999.
6. Crawford et al., *Neurosci. Lett.*, 266:193, 1999.
7. Lilius et al., *Neurosci. Lett.*, 277:29, 1999.
8. Baker et al., *Neurosci. Lett.*, 285:147, 2000.
9. Kwon et al., *Neurosci. Lett.*, 284:77, 2000.
10. Baker et al., *Hum. Mol. Genet.*, 8:711, 1999.
11. Hecker and Roux, *Biotechniques*, 20:478, 1996.
12. Jicha et al., *J. Neurosci.*, 19:7486, 1999.
13. Ausubel et al., *Current Protocols in Molecular Biology* (New York: John Wiley and Sons, New York, 1997).
14. Altschul et al., *Nucleic Acids Res.*, 25:3389, 1997.
15. Y. Oda, *Pathol. Int.*, 49:921, 1999.
16. Gu et al., *J. Neurochem.*, 67:1235, 1996.
17. Saunders et al., *Neurology*, 43:1467, 1993.
18. Corder et al., *Cell Mol. Life Sci.*, 54:928, 1998.
19. Jin and Saitoh, *Drugs Aging*, 6:136, 1995.
20. Wenham et al., *Lancet*, 337:1158, 1991.
21. R. Weiss, Science, 254:1292, 1991.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. An isolated nucleic acid encoding saitohin (STH), wherein the isolated nucleic acid consists of (i) the nucleic acid encoding saitohin-Q (STH-Q) or (ii) the nucleic acid encoding saitohin-R (STH-R), wherein saitohin-Q (STH-Q) consists of the amino acid sequence set forth in SEQ ID NO: 3 and saitohin-R (STH-R) consists of the amino acid sequence set forth in SEQ ID NO: 4, or (iii) the nucleic acid that is fully complementary to (i) or (ii).

2. The nucleic acid of claim 1, which is DNA, cDNA, or RNA.

3. The nucleic acid of claim 1, which consists of the saitohin-Q (STH-Q) allele set forth in SEQ ID NO:1.

4. The nucleic acid of claims which consists of the saitohin-R (STH-R) allele set forth in SEQ ID NO:2.

5. The nucleic acid of claim 1, which encodes a protein comprising the amino acid sequence set forth in SEQ ID NO:3.

6. The nucleic acid of claim 1, which encodes a protein comprising the amino acid sequence set forth in SEQ ID NO:4.

7. An isolated nucleic acid consisting of a contiguous fragment of the nucleotide sequence set forth in SEQ ID NO:1 or in SEQ ID NO:2, wherein the contiguous fragment has a length of at least 8 nucleotides.

8. The isolated nucleic acid of claim 7, which consists of a contiguous fragment of the nucleotide sequence set forth in SEQ ID NO:1.

9. The isolated nucleic acid of claim 7, which consists of a contiguous fragment of the nucleotide sequence set forth in SEQ ID NO:2.

10. The isolated nucleic acid of claim 7, wherein the contiguous fragment has a length of 8 to 30 nucleotides.

11. A labeled nucleic acid probe consisting of the isolated nucleic acid of claim 7, and a label.

12. The labeled nucleic acid probe of claim 11, wherein the label is a radioactive label, biotin, or a fluorescent label.

13. A purified saitohin protein comprising the saitohin-Q (STH-Q) amino acid sequence set forth in SEQ ID NO:3 or the saitohin-R (STH-R) amino acid sequence set forth in SEQ ID NO:4.

14. The protein of claim 13, which is the saitohin-Q (STH-Q) isoform set forth in SEQ ID NO:3.

15. The protein of claim 13, comprising the amino acid sequence set forth in SEQ ID NO:3.

16. The protein of claim 13, encoded by the nucleotide sequence set forth in SEQ ID NO:1.

17. The protein of claim 13, which is the saitohin-R (STH-R) isoform set forth in SEQ ID NO:4.

18. The protein of claim 13, comprising the amino acid sequence set forth in SEQ ID NO:4.

19. The protein of claim 13, encoded by the nucleotide sequence set forth in SEQ ID NO:2.

20. A vector comprising nucleic acid encoding saitohin (STH), wherein the nucleic acid encoding saitohin (STH) consists of the nucleic acid of claim 1.

21. A vector comprising nucleic acid encoding saitohin (STH), wherein the nucleic acid encoding saitohin (STH) consists of the nucleic acid of claim 2.

22. A vector comprising nucleic acid encoding saitohin (STH), wherein the nucleic acid encoding saitohin (STH) consists of the nucleic acid of claim 3.

23. A vector comprising nucleic acid encoding saitohin (STH), wherein the nucleic acid encoding saitohin (STH) consists of the nucleic acid of claim 4.

24. A vector comprising nucleic acid encoding saitohin (STH), wherein the nucleic acid encoding saitohin (STH) consists of the nucleic acid of claim 5.

25. A vector comprising nucleic acid encoding saitohin (STH), wherein the nucleic acid encoding saitohin (STH) consists of the nucleic acid of claim 6.

26. A host cell transformed with the vector of claim 20, wherein the host cell is an isolated or cultured host cell.

27. A host cell transformed with the vector of claim 21, wherein the host cell is an isolated or cultured host cell.

28. A host cell transformed with the vector of claim 22, wherein the host cell is an isolated or cultured host cell.

29. A host cell transformed with the vector of claim 23, wherein the host cell is an isolated or cultured host cell.

30. A host cell transformed with the vector of claim 24, wherein the host cell is an isolated or cultured host cell.

31. A host cell transformed with the vector of claim 25, wherein the host cell is an isolated or cultured host cell.

32. A method of making saitohin (STH) protein, comprising the steps of:
   (a) introducing into a host cell a nucleic acid sequence encoding STH,
   (b) maintaining the host cell under conditions such that the nucleic acid sequence is expressed to produce STH protein, and
   (c) recovering the STH protein, wherein sairohin (STH) protein comprises the (i) sairohin-Q (STH-Q) amino acid sequence set forth in SEQ ID NO:3 or the (ii) saitohin-R (STH-R) amino acid sequence set forth in SEQ ID NO:4.

33. The method of claim 32, wherein the STH protein is the STH-Q isoform set forth in SEQ ID NO:3.

34. The method of claim 32, wherein the STH protein is the STH-R isoform set forth in SEQ ID NO:4.

* * * * *